US009441020B2

(12) United States Patent
Ajjawi et al.

(10) Patent No.: US 9,441,020 B2
(45) Date of Patent: Sep. 13, 2016

(54) BIOMASS PRODUCTIVITY REGULATOR

(71) Applicant: Synthetic Genomics, Inc., La Jolla, CA (US)

(72) Inventors: Imad Ajjawi, La Jolla, CA (US); Moena Aqui, San Diego, CA (US); Carlos Chavez-Torres, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/586,612

(22) Filed: Dec. 30, 2014

(65) Prior Publication Data

US 2015/0183838 A1    Jul. 2, 2015

Related U.S. Application Data

(60) Provisional application No. 61/922,388, filed on Dec. 31, 2013.

(51) Int. Cl.
| | | |
|---|---|---|
| *C12P 7/64* | (2006.01) | |
| *C12N 1/13* | (2006.01) | |
| *C12N 15/79* | (2006.01) | |
| *C07H 21/00* | (2006.01) | |
| *C07K 14/405* | (2006.01) | |
| *C12N 15/82* | (2006.01) | |

(52) U.S. Cl.
CPC ............ *C07K 14/405* (2013.01); *C12N 15/79* (2013.01); *C12N 15/8247* (2013.01); *C12N 15/8261* (2013.01); *C12P 7/6463* (2013.01)

(58) Field of Classification Search
None
See application file for complete search history.

(56) References Cited

U.S. PATENT DOCUMENTS

| | | |
|---|---|---|
| 2011/0045533 A1 | 2/2011 | Cadoret et al. |
| 2012/0277418 A1 | 11/2012 | Kilian et al. |
| 2013/0333074 A1 | 12/2013 | Mock et al. |
| 2014/0220638 A1 | 8/2014 | Bailey et al. |

OTHER PUBLICATIONS

Sang, H., "Prospects for transgenesis in the chick", Mechanisms of Development 121:1179-1186, 2004.*
GenBank Accession No. JU967096, "TSA: Nannochloropsis gaditana CCMP526 NGA_Contig1486 mRNA sequence", May 2012, 1 page.*
Carpinelli et al.: "*Chromosome Scale Genome Assembly and Transcriptome Profiling of Nannochloropsis gaditana in Nitrogen Depletion,*"; Molecular Plant, Aug. 21, 2013, vol. 7, No. 2, pp. 323-335.
Radakovits et al.: *Draft genome sequence and genetic transformation of the oleaginous alga Nannochloropis gaditana,*;Nature Communications, Feb. 21, 2012, vol. 3, No. 686, pp. 1-10.
International Search Report issued on Apr. 24, 2015 Regarding PCT/US2014/072831.

* cited by examiner

*Primary Examiner* — David J Steadman
(74) *Attorney, Agent, or Firm* — DLA Piper LLP (US)

(57) ABSTRACT

The disclosure generally relates to methods and materials for modulating cell productivity. In particular, the present disclosure provides polynucleotides and polypeptides that when overexpressed in microorganisms result in increased in productivity, such as increased biomass productivity. Also disclosed are methods of using the polynucleotides and polypeptides to modulate or increase productivity of host cells such as, for example, algal or heterokont cells. Genetically engineered host cells, such as algal and heterokont cells having increased biomass productivity and bioproducts derived from such host cells are also disclosed.

19 Claims, 5 Drawing Sheets

FIG. 1A-C

SEQUENCE LISTING

```
<160> NUMBER OF SEQ ID NOS: 23

<210> SEQ ID NO 1
<211> LENGTH: 138
<212> TYPE: DNA
<213> ORGANISM: Nannochloropsis gaditana

<400> SEQUENCE: 1
cctggacgct ggacggctga ggaacatatg ttgtttctta ggggtctgca attacacggt      60
aaatcatgga agaaaatatc cgagattgtt acaacgcgga cagtggtcca aattcgtaca     120
catgcccaga aataccctt                                                   138

<210> SEQ ID NO 2
<211> LENGTH: 46
<212> TYPE: PRT
<213> ORGANISM: Nannochloropsis gaditana

<400> SEQUENCE: 2

Pro Gly Arg Trp Thr Ala Glu Glu His Met Leu Phe Leu Arg Gly Leu
1               5                   10                  15
```

Gln Leu His Gly Lys Ser Trp Lys Lys Ile Ser Glu Ile Val Thr Thr
            20                  25                  30

Arg Thr Val Val Gln Ile Arg Thr His Ala Gln Lys Tyr Leu
        35                  40                  45

<210> SEQ ID NO 3
<211> LENGTH: 1347
<212> TYPE: DNA
<213> ORGANISM: Nannochloropsis gaditana

<400> SEQUENCE: 3

| | | | | | |
|---|---|---|---|---|---|
| atggagactt | cgacgagaaa | aggctttcat | gaacgcagtg | acgcacgatt | tccagctgga | 60 |
| gcgcttcatg | attccatgaa | cttgacatca | aatgattcat | tcagaagctc | tcagtttggc | 120 |
| aaggaaggcg | ccttcaacga | agtcaagaaa | gaccctggac | gctggacggc | tgaggaacat | 180 |
| atgttgtttc | ttaggggtct | gcaattacac | ggtaaatcat | ggaagaaaat | atccgagatt | 240 |
| gttacaacgc | ggacagtggt | ccaaattcgt | acacatgccc | agaaatacct | tataaagttg | 300 |
| gaaaaggcta | gaaaggctgg | tcatcagggt | gtcttaatga | tggatgggaa | aggcgtcgat | 360 |
| aacactgaac | gtcgaggcac | ttccaagaaa | tcatctttgt | ccacgaaaac | ggtgagtttc | 420 |
| acatctactt | ctcctgaatc | ttctgttctc | gagcagaaga | gacagaaaaa | tgagccagcg | 480 |
| gctcacctgc | caggtcctgt | gcagcatact | actgtacgcc | cttttgcacc | tgtcacaaga | 540 |
| gccgcacctt | caggctgccc | cccaactgcg | cccgcaggat | tcgtgccatg | gatggtaggc | 600 |
| ccatacgctt | gtgtccctcc | aacatactac | aacatgcaaa | tgatggccca | tggatatgac | 660 |
| tttggtgctc | cgctggtatc | gccatcatca | caatatcgtg | cgagtttttc | aaatcccctg | 720 |
| tctgcacccg | aggaaattg | ccaagagcag | gacttgggac | taaacgcacc | tcaatctgtg | 780 |
| agaatgccct | tggaggctga | aatggctgca | caaattcatt | acctgggcat | tgacaacgag | 840 |
| gaaactatcg | cgcaaaatca | gccaaattcc | tataagcgtc | tacgtgtccc | cgcaggtctg | 900 |
| gctatggcga | cgcctgccgc | ggtttctacg | gcacaatcct | ctcattgtaa | agtctacgtt | 960 |
| gccccgcagc | agtcatgcac | ctcgccttct | gatatgactc | cgactctaac | cgcatcagcc | 1020 |
| ttacatcagc | caccgcaggg | atctctttgc | ccgttcatga | catcaaatcc | tttagacgag | 1080 |
| ctcatgcaaa | gcctgtcgca | ggagaatctt | tcttcctcct | gctcctcgac | ctctccatct | 1140 |
| atcgcacccg | aagttgatgt | acccagcatg | catgacatac | tcatttggga | cctaaatggg | 1200 |
| aaacatagcc | gccttcttc | ccttagctcc | tgggacgagg | agggcttcga | tggagtctca | 1260 |
| acctcatctt | cccctgcaag | cattgacaat | cacgttgttt | gccaacctcc | ggatttgagc | 1320 |
| gagcttcagt | atgcgaaagc | tgcgtga | | | | 1347 |

<210> SEQ ID NO 4
<211> LENGTH: 448
<212> TYPE: PRT
<213> ORGANISM: Nannochloropsis gaditana

<400> SEQUENCE: 4

Met Glu Thr Ser Thr Arg Lys Gly Phe His Glu Arg Ser Asp Ala Arg
1               5                   10                  15

Phe Pro Ala Gly Ala Leu His Asp Ser Met Asn Leu Thr Ser Asn Asp
            20                  25                  30

Ser Phe Arg Ser Ser Gln Phe Gly Lys Glu Gly Ala Phe Asn Glu Val
        35                  40                  45

Lys Lys Asp Pro Gly Arg Trp Thr Ala Glu Glu His Met Leu Phe Leu

```
            50                  55                  60
Arg Gly Leu Gln Leu His Gly Lys Ser Trp Lys Lys Ile Ser Glu Ile
65                  70                  75                  80

Val Thr Thr Arg Thr Val Val Gln Ile Arg Thr His Ala Gln Lys Tyr
                85                  90                  95

Leu Ile Lys Leu Glu Lys Ala Arg Lys Ala Gly His Gln Gly Val Leu
            100                 105                 110

Met Met Asp Gly Lys Gly Val Asp Asn Thr Glu Arg Arg Gly Thr Ser
            115                 120                 125

Lys Lys Ser Ser Leu Ser Thr Glu Thr Val Ser Phe Thr Ser Thr Ser
        130                 135                 140

Pro Glu Ser Ser Val Leu Glu Gln Lys Arg Gln Lys Asn Glu Pro Ala
145                 150                 155                 160

Ala His Leu Pro Gly Pro Val Gln His Thr Thr Val Arg Pro Phe Ala
                165                 170                 175

Pro Val Thr Arg Ala Ala Pro Ser Gly Cys Pro Pro Thr Ala Pro Ala
            180                 185                 190

Gly Phe Val Pro Trp Met Val Gly Pro Tyr Ala Cys Val Pro Pro Thr
        195                 200                 205

Tyr Tyr Asn Met Gln Met Met Ala His Gly Tyr Asp Phe Gly Ala Pro
210                 215                 220

Leu Val Ser Pro Ser Ser Gln Tyr Arg Ala Ser Phe Ser Asn Pro Leu
225                 230                 235                 240

Ser Ala Pro Gly Gly Asn Cys Gln Glu Gln Asp Leu Gly Leu Asn Ala
                245                 250                 255

Pro Gln Ser Val Arg Met Pro Leu Glu Ala Glu Met Ala Ala Gln Ile
            260                 265                 270

His Tyr Leu Gly Ile Asp Asn Glu Glu Thr Ile Ala Gln Asn Gln Pro
        275                 280                 285

Asn Ser Tyr Lys Arg Leu Arg Val Pro Ala Gly Leu Ala Met Ala Thr
290                 295                 300

Pro Ala Ala Val Ser Thr Ala Gln Ser Ser His Cys Lys Val Tyr Val
305                 310                 315                 320

Ala Pro Gln Gln Ser Cys Thr Ser Pro Ser Asp Met Thr Pro Thr Leu
                325                 330                 335

Thr Ala Ser Ala Leu His Gln Pro Pro Gln Gly Ser Leu Cys Pro Phe
            340                 345                 350

Met Thr Ser Asn Pro Leu Asp Glu Leu Met Gln Ser Leu Ser Gln Glu
        355                 360                 365

Asn Leu Ser Ser Cys Ser Ser Thr Ser Pro Ser Ile Ala Pro Glu
370                 375                 380

Val Asp Val Pro Ser Met His Asp Ile Leu Ile Trp Asp Leu Asn Gly
385                 390                 395                 400

Lys His Ser Arg Pro Ser Ser Leu Ser Ser Trp Asp Glu Glu Gly Phe
                405                 410                 415

Asp Gly Val Ser Thr Ser Ser Ser Pro Ala Ser Ile Asp Asn His Val
            420                 425                 430

Val Cys Gln Pro Pro Asp Leu Ser Glu Leu Gln Tyr Ala Lys Ala Ala
        435                 440                 445

<210> SEQ ID NO 5
<211> LENGTH: 927
<212> TYPE: DNA
<213> ORGANISM: Nannochloropsis gaditana
```

<400> SEQUENCE: 5

```
ctactctcca actgagacga aatttatagc gccatctcgc ttctgactac caggcttagg      60
aaggcctcat cacaagctgg atcggttcga attaagcagg cactgaagcc aagcttgcaa     120
gacagccacc ttttaattct ctcaaaacac tttctcaatt cagcccggta aatatgccga     180
ttcacagcgg ccaagataga ggggaggtta gcaagaatgt tgcgatccct ccccagtcgt     240
tgcctcgcac acaacctagg acttcacctt tccatgaaaa attgagaagt gaatattggt     300
tttcttacgg catatcagat gaaatcatga cccctaaaca tgaagagctg caggcaaaac     360
acctgctctg gacgagcacg atgaaatctc gagaacccgc cgtacttcag ttgatcccgc     420
atgatgacgg ccgccattga aataagccac ctcactttat tctagcaccg atttccaccg     480
ttgtgagggc cgaacgagga caatttcgtg cgaaacaagc acgaacgcgc acacgattag     540
taggacagac gagcagatcg atggcatgcg gcacggtctc gcgttctcgg cgaccaggac     600
aacggagcag agggaggcct gccgagttcc gaggggcatt ttagtccaaa attgtgttga     660
cacgtgaaca agtggcttga aaagaggaag gaaatgcctg ggtttccctt cgagagcggg     720
aactcgcttg tgcgtcatcc tagctaccca tggtcccttt gtggggagg ctgtttcgtc      780
ctaccgaatg tgtggcgctc catgcatctt ctgcctccca aaccaccaac atgagcacgc     840
gaaggaagga gaaaaagtg gccgcaacgt tctcttctca tatttattgt ctcatcacaa      900
acataggtac ataatacaac aatcatg                                         927
```

<210> SEQ ID NO 6
<211> LENGTH: 923
<212> TYPE: DNA
<213> ORGANISM: Nannochloropsis gaditana

<400> SEQUENCE: 6

```
aaagttgaaa atgctaacag tgaagtgata tcctttttta atggagtgtt gaggtgaagt      60
ctagcatcgt agggggaaaac aggattctgt gtcttccatt ctactccttg ataaagcgaa    120
gaaatccgac aaaaccaaag agattgttca agtttaagat tgtaagcgt acaactatga      180
acttcttctc tttgtaggcc tgagtggtcg tatgcatacg attcatgaag tgaatcagta     240
tcgctggatt tgcttagga gtaaagcaca actaagaaaa tatgctgcct ggcaggcatc      300
ctgagacatg aggcaagcga cgtagcaatt gaatcctaat ttaagccagg gcatctgtat     360
gactctgtta gttaattgat gaaccaatga gctttaaaaa aaaatcgttg cgcgtaatgt     420
agttttaatt ctccgccttg aggtgcgggg ccatttcgga caaggttctt tggacggaga     480
tggcagcatg tgtcccttct ccaaattggt ccgtgtggta gttgagatgc tgccttaaaa     540
ttctgctcgg tcatcctgcc ttcgcattca ctcctttcga gctgtcgggt tcctcacgag     600
gcctccggga gcggattgcg cagaaaggcg acccggagac acagagacca tacaccgact     660
aaattgcact ggacgatacg gcatggcgac gacgatggcc aagcattgct acgtgattat     720
tcgccttgtc attcagggag aaatgatgac atgtgtggga cggtctttat atgggaagag     780
ggcatgaaaa taacatggcc tggcgggatg gagcgtcaca cctgtgtatg cgttcgatcc     840
acaagcaact caccatttgc gtcggggcct gtctccaatc tgctttaggc tacttttctc     900
taatttagcc tattctatac aga                                             923
```

<210> SEQ ID NO 7
<211> LENGTH: 1000
<212> TYPE: DNA

<213> ORGANISM: Nannochloropsis gaditana

<400> SEQUENCE: 7

| | | | | | |
|---|---|---|---|---|---|
| aataagcata | catcatatga | atacaattca | gcttaaattt | atcatacaaa | gatgtaagtg | 60 |
| cagcgtgggt | ctgtaacgat | cgggcgtaat | ttaagataat | gcgagggacc | ggggaggtt | 120 |
| ttggaacgga | atgaggaatg | ggtcatggcc | cataataata | atatgggttt | ggtcgcctcg | 180 |
| cacagcaacc | gtacgtgcga | aaaaggaaca | gatccattta | ataagttgaa | cgttattctt | 240 |
| tcctatgcaa | tgcgtgtatc | ggaggcgaga | gcaagtcata | ggtggctgcg | cacaataatt | 300 |
| gagtctcagc | tgagcgccgt | ccgcgggtgg | tgtgagtggt | catcctcctc | ccggcctatc | 360 |
| gctcacatcg | cctctcaatg | gtggtggtgg | ggcctgatat | gacctcaatg | ccgacccata | 420 |
| ttaaaaccca | gtaaagcatt | caccaacgaa | cgagggctc | ttttgtgtgt | gttttgagta | 480 |
| tgatttttaca | cctctttgtg | catctctctg | gtcttccttg | gttcccgtag | tttgggcatc | 540 |
| atcactcacg | cttccctcga | ccttcgttct | tcctttacaa | ccccgacaca | ggtcagagtt | 600 |
| ggagtaatca | aaaaggggt | gcacgaatga | gatacattag | attttgacag | atatcctttt | 660 |
| actggagagg | gttcaaggga | tcaaatgaac | agcgggcgtt | ggcaatctag | ggagggatcg | 720 |
| gaggttggca | gcgagcgaaa | gcgtgtccat | ccttttggct | gtcacacctc | acgaaccaac | 780 |
| tgttagcagg | ccagcacaga | tgacatacga | gaatctttat | tatatcgtag | accttatgtg | 840 |
| gatgaccttt | ggtgctgtgt | gtctggcaat | gaacctgaag | gcttgatagg | gaggtggctc | 900 |
| ccgtaaaccc | tttgtccttt | ccacgctgag | tctcccccgc | actgtccttt | atacaaattg | 960 |
| ttacagtcat | ctgcaggcgg | tttttctttg | gcaggcaaac | | | 1000 |

<210> SEQ ID NO 8
<211> LENGTH: 163
<212> TYPE: DNA
<213> ORGANISM: Nannochloropsis gaditana

<400> SEQUENCE: 8

| | | | | | |
|---|---|---|---|---|---|
| gagtcaaggg | ggaaggtgca | tagtgtgcaa | caacagcatt | aacgtcaaag | aaaactgcac | 60 |
| gttcaagccc | gcgtgaacct | gccggtcttc | tgatcgccta | catatagcag | atactagttg | 120 |
| tactttttt | tccaaaggga | acattcatgt | atcaatttga | aat | | 163 |

<210> SEQ ID NO 9
<211> LENGTH: 1504
<212> TYPE: DNA
<213> ORGANISM: Tetraselmis sp.

<400> SEQUENCE: 9

| | | | | | |
|---|---|---|---|---|---|
| caccctcacc | tctaaggatt | actggtaccc | caacatccag | tagcgccccc | ggccagctac | 60 |
| ggtgacccaa | aaagctagta | ctttatctga | tagtggaaga | actctaccgg | atgtatatac | 120 |
| agcaggatat | tcgtagccct | gtcacatgga | tgccagcaag | acaccggtca | ttctgtcatc | 180 |
| ttcgtaccat | ataatgtcgg | cctacgggta | ccaagaggcg | gtatgtacag | gcccccgga | 240 |
| cggcgcggat | gtcaggcagg | cagcaaggat | gtgtacgaat | gcacccgtgt | acatctcgcg | 300 |
| ctccatcggt | agccgctgct | atatagtcgc | tagccacttt | ttgtcgtccc | gccggcatta | 360 |
| tgacatatag | cgactacata | gcgaccacac | cagatatatc | tagttgctac | gttagagcga | 420 |
| cggcacgacg | tacaatccta | ctactgctgt | cgtcgtgtac | tgtgccgtgc | catgttgctg | 480 |
| tgttgcgtct | agctcatgta | atccatgttg | ctgtgtttca | gcgcgcgcac | accgcgagac | 540 |
| cgacgacgct | cgcgcgggat | ggtcagatta | tttttagtac | agtacagtga | ggcagaaaca | 600 |

-continued

```
catcaaagct tcggccgatg tcccggggcg aactttacat cacagcagaa tcgatttctc    660
aggtcgaatt gtcgtcatat agcgactata taaatgttct taattacatc agggattgca    720
caaatgcgca ctacaaacta tattattgtt cttaaaaata tacaaaaaga tgaaaaaagt    780
atcttcgtcc gcgcattatt accgtatgag caccgtgcg agtccgagcc ctcccggtgc     840
tagtggatcc aggacacgac tagcagtgat tacatgagct agacgcaaca ttcaagaaat    900
ccacacagaa atccagaagg aaataagcag taccagtatt aagtactcct ggtggtaaca    960
ccgactatac tggtctactg ctgacgcgac ctatcacgta tattaacata ttcaatacccc  1020
gcatacatgg catatacgac ggataacacc aggtctgtat ctgtaatcaa aattatattc   1080
catatagttg ttcatccttt accggtactg gtagtgaatt acaaaaagga caattctcta   1140
gaattagaaa atcaacacat caagccgcct aaagaaaatc aacacatcct ttaccggtag   1200
agcatacgat gaatatattc gctgttacat ggtttcttgc tgtcggagcg cgcgacggcg   1260
acggcacggc tcatcgggcg tcgtatcgga agtcaggggc gcgcaaaact ccgagagcac   1320
atcagcagca catccgccgg agtattacgc aacatatcct tacagagttg cgcacggtgg   1380
cgtcgtatag tgcatcaaca acatagcaac ccctactttc tggcaaccct tccgagagct   1440
gaggatagtc gcgtcacccc acttccaact tccgtcttcc gtctcaacca ctacacccga   1500
cacc                                                                1504
```

<210> SEQ ID NO 10
<211> LENGTH: 1222
<212> TYPE: DNA
<213> ORGANISM: Tetraselmis sp.

<400> SEQUENCE: 10

```
gaggcctatc ctcgctgctc ataccaccat tcatccacaa atagcagtag ccagcacctg    60
ttgccctctg tgcgcaagtg tgtcagatag gactgcaaat atgaaaacca gccaaattcc    120
tgtactggaa ttggttactc tccactttt tttaggtaga actgtaacca tatcttgcaa     180
aaataccaac aatgcaagga aggagacatt gtgcaggaat acatgctacc taattctggg   240
ggcgacgttc tgaggttttc agttgcggac agcaatgcag cttcaagaca acaatggcat   300
gccttgtccc tttccgcaca tggttatggc atgaatagca agatgttcac tagcgggctg   360
ctgccattca ctgattgttg atgaatgcgc acatttctct gggtagtgga gggtaatttt   420
ggcgttttgg gtattatccg aaatgcctag tttccaacat cgtggatatg ctcttcagtc   480
tcattgtagc atgctgcccg cctgttttga atgcagtgg gttaaattgg tgcagaagag    540
ggggcagatt ctgtcacatg caactaaaca tcaagggaca atgacaaaat tgtttcccac   600
taggacgata aatccgcact atataatgag acagtgagtg cttttccacc aacctccatg   660
ttgatagaaa tgccaacacc agatcgatgg gcaacattat cggcactcgg ccatgtaggc   720
actcatcgca aatcccggca ctggtggtgc gtgttgggct gccactgtaa gcgcatgccc   780
gctgcagaga ctccactgat gaaggcgctc cagcgaagat ataagcgaaa actgtgacac   840
agcaacccac cagttgactt cactggcaag aagtaccttc tttgttagca tccagtagac   900
tgacctcaat atgcactcgc attaattcga ctataacgaa tcatggaact accgaagcat   960
gcaatacgta acatatccgc tgtgtaagta taaatgagcg gtgcgcatgt gctatgatgt   1020
tgcgcagcat agtttatgag ttgttattaa ggaggttgct actgggcttg ccaaatgatt   1080
cagttctgtg agccagatcc ttgagatttg gtgtcgcgac gagcacatgt aaacctttaa   1140
```

```
aaccgttata tcacttaatt aatgacacag catatgaaac ctagcttaag ttggtaccgt    1200
cgtggacaag tacaagatcg cc                                            1222

<210> SEQ ID NO 11
<211> LENGTH: 378
<212> TYPE: DNA
<213> ORGANISM: Artificial Sequence
<220> FEATURE:
<223> OTHER INFORMATION: ble gene

<400> SEQUENCE: 11
atgttggcca agctgacgtc ggcggttccg gtcctgacag cgcgtgacgt ggccggagcg      60
gtggagtttt ggactgaccg gctcgggttt agccgggact tcgtcgagga cgatttcgct    120
ggcgtagtac gcgatgacgt gaccctcttt atctcggcgg tgcaagacca ggtcgtcccc    180
gacaacacgc tggcttgggt ctgggtgcga ggccttgatg agctgtacgc cgagtggtcc    240
gaggtggttt ccaccaactt ccgcgacgcg agcggtcctg ccatgaccga gattggcgaa    300
cagccgtggg ggagggagtt cgcactccgc gacccagcag gcaattgcgt gcacttcgtc    360
gccgaagagc aggattag                                                  378

<210> SEQ ID NO 12
<211> LENGTH: 716
<212> TYPE: DNA
<213> ORGANISM: Tetraselmis sp.

<400> SEQUENCE: 12
cgtttctgat cctgggcctt ccccgcccgc tgtaccgccg cgcccgcgct cttcgctctt      60
cgctcttcgc gattcagctc gccgccgcca ccgcgaacta gatgcccgcc cctgcagtt     120 agcacaaccg cgcccggct agtattgcat caaccagcca ggtctggcat atggtggtac     180
cacacgtagt cgaagcaggt accccgcgtt tcgagttatc ccctggcccc ctttggtatc    240
ggatcgccgt tggcctctgg gtccagggta acgacgtgcc gcaggttgct gcagcctcgt    300
ttgaaccggc ccgagggggc ccgcccgcca gttgatgcac ggttcgcgac ccggcgcctc    360
tccgaaatat actgttcccc tctgctagct ttggtagtca ctagataccg tccggcgacg    420 tgccccctgtc gggccctggg cgacagccca gcacgtccca gtcaaactcc ggctgaccgg    480
acgctcacac acagctgact gaccctccga ccccctctctt tcgggtcaca ccatcccggc    540
ccgcggaccg catagcctgt ggctcctctt ttcgccatat ctcttcttgc gtaatcttgc    600
acgcaattcc ggcgcctctg ccccgtacat cgctcctgtc tgccttttttt gccccactct    660 gaccccctcc tgcatgtgcg ctttgctctc atagagctct tacgaagaaa ggcacc        716

<210> SEQ ID NO 13
<211> LENGTH: 1011
<212> TYPE: DNA
<213> ORGANISM: Tetraselmis sp.

<400> SEQUENCE: 13
agcaagcgct gtgcaatcaa atcaatgctg tctgcgaatg gcgcgtcgtg gcagcggtgc      60
atgtgccgga gcaaggtttg cgcgcacagg gttggcggtg cacgactgtg gctgttgggc    120 agcaagggg gggtagcaca gtccttgacg cggtgccaag gcggtcctgt ccgtcaggtg    180
agggctgctt ggcctgtgag ctggaggcgc cactgctagc aggacgccca cgatagagta    240
agcgctttct tctggcgcaa catttaatca cacttctgta tctcctttc cctgccagtc     300 tgcttgctgg cgcacttgta ccgtttagtg tggttgtacg ctcgcttcct ccctcagccc    360
```

```
gcggcaggag tgctagggaa attcttgcac agagcacaac cgctctcaat gtgacgttga    420
tcggcactct ttcccatgga cagtcaactt ccactggcat tgtttaaatg ctattagcca    480
cttccttaca cgcgaaaaat agcacaagaa ataagcgtcc ctactactca ccgcaccgtc    540
gtgaccatac atcactggtt ccatattgag ctcaggaact cttcagcgcg ttgcccgacg    600
ggagtgccag ggtgcggccg ccatccaaca tgaaactctg cccggtgatg aagccagatg    660
tgctggagga tcccaggaaa ataccgcct cggcaacgtc tgtgggctgc ctgcaatcag     720
aagtgcacag caattgagga tgctgccaaa tggttgatgt gaagtcaggg gagttttgtc    780
atctgcagta tggcacaggg ggggtagatt gagagtctca cccgatgcgg cccagtggat    840
ggcagctagc agactcagcc aggaaggtct cagtgccttc agtcccaagc ccagcacttg    900
ccaaaaagtc ggtctcaatc ctggcggttc acagcagcac atcttgaatg ttacgcgtat    960
gtgatggggc ctggatgggc agggctccaa ccaccaaaca cgaccatttg g             1011
```

<210> SEQ ID NO 14
<211> LENGTH: 816
<212> TYPE: DNA
<213> ORGANISM: Cyclotella sp.

<400> SEQUENCE: 14

```
attgttcaag ggccacaatc tgccacaatg aaagctgaag tggaggccaa gcgaatgtag     60
tgacagtttt gacaccatcc ttgaagtaaa actatagac gtactccaag aagaagaaga    120
acgaatttga ttaagtacgt cacagtgatg tcatcctgaa gtatgcctgg ccatcgtttc    180
cactctccgc gacgttacga cttcgtgtgt cggcatttcg tcagtggttt tgtgctatac    240
atgacatcat ccaaaatcgt cacaaagatc caaagatat aagagggagg tggagttcgc    300
attggatgta gaggagcttc cataataaaa aaatatatcg atacaagtaa cattttctac    360
aacgacttta cgtaagaaaa aaatcgtaat ttcaaatata ttaccaattt tacttttgat    420
atcgcagccc ttgttccccg atatgtatct ttcaacgtgc tgacgtacgc ccctacgagc    480
cgttgatggc cgaaatcttc gtggatgtgt atcgtaaaat tataaaatat gaaagtatgg    540
taggtggtag gtacggtatt gtacgataca tctgtcttgt gatgcgttca ttcgccactg    600
gcgtacttcc atcaaaaact cacccaaagg cccgctcctg ccagccacgg tcgtcttttg    660
tggacgtcaa caaccttcaa tatcgagttc gttgtgattg acgcatcctc tccgaattgg    720
cattgcgttg ttgaacactc ttaacttttcg gcatttcctc acgatagtca taaatcaact    780
gcacatcctc gtcgactttg aaaacgacat caaacc                              816
```

<210> SEQ ID NO 15
<211> LENGTH: 822
<212> TYPE: DNA
<213> ORGANISM: Nannochloropsis sp.

<400> SEQUENCE: 15

```
ggcataaagg acggcaagga agaaaagaa agaaagaaaa ggacacttat agcatagttt      60
gaagttataa gtagtcgcaa tctgtgtgca gccgacagat gcttttttttt tccgtttggc    120 aggaggtgta gggatgtcga agaccagtcc agctagtatc tatcctacaa gtcaatcatg    180
ctgcgacaaa aatttctcgc acgaggcctc tcgataaaca aaactttaaa agcacacttc    240
attgtcatgc agagtaataa ctcttccgcg tcgatcaatt tatcaatctc tatcatttcc    300 gccccttttcc ttgcatagag caagaaaagc gacccggatg aggataacat gtcctgcgcc    360
```

```
agtagtgtgg cattgcctgt ctctcattta cacgtactga agcataatg cacgcgcata    420 ccaatatttt tcgtgtacgg agatgaagag acgcgacacg taagatcacg agaaggcgag    480
cacggttgcc aatggcagac gcgctagtct ccattatcgc gttgttcggt agcttgctgc    540
atgtcttcag tggcactata tccactctgc ctcgtcttct acacgagggc cacatcggtg    600
caagttcgaa aaatcatatc tcaatcttca gatccttttcc agaaacggtg ctcaggcggg    660
aaagtgaagg ttttctactc tagtggctac cccaattctc tccgactgtc gcagacggtc    720
cttcgttgcg cacgcaccgc gcactacctc tgaaattcga caaccgaagt tcaattttac    780
atctaacttc tttcccattc tctcaccaaa agcctagctt ac                       822
```

<210> SEQ ID NO 16
<211> LENGTH: 1620
<212> TYPE: DNA
<213> ORGANISM: Nannochloropsis gaditana

<400> SEQUENCE: 16

```
atggagactt cgacgagaaa aggctttcat gaacgcagtg acgcacgatt tcccgctgga     60
gcgcttcatg attccatgaa cttgacatca aatgattcat tcagaagctc tcagtttggc    120
aaggaaggcg ccttcaacga aggtaaatga gtaaaacaaa tattggtcga gatattttaa    180
aatctcgcgt tcacaccgc aattggaacc ctgctctgca atcaaattgc gaactttgtg     240
acataaaaca cagtctgcta acgcctttc actatactca taccatcata cgtagtcaag     300
aaagaccctg gacgctggac ggctgaggaa catatgttgt ttcttagggg tctgcaatta    360
cacggtaaat catggaagaa aatatccgag attgttacaa cgcggacagt ggtccaaatt    420
cgtacacatg cccagaaata ccttataaag ttggaaaagg ctagaaaggc tggtcatcag    480
ggtgtcttaa tgatggatgg gaaaggcgtc gataacactg aacgtcgagg cacttccaag    540
gtacgtcgct taaaatccaa tcaaaaattg tcatttttt cactattgat gcgtcttttc      600
atgcttgaag gcttggcctt atgttgtttt acatttaaga ctctcttctt taaataccag    660
aaatcatctt tgtccacgga aacggtgagt ttcacatcta cttctcctga atcttctgtt    720
ctcgagcaaa agagacagaa aaatgagcca gcggctcacc tgccaggtcc tgtgcagcat    780
actactgtac gccctttgc acctgtcaca agagccgcac cttcaggctg ccccccaact     840
gcgcccgcag gattcgtgcc atggatggta ggcccatacg cttgtgtccc tccaacatac    900
tacaacatgc aaatgatggc ccatggatat gactttggtg ctccgctggt atcgccatca    960
tcacaatatc gtgcgagttt ttcaaatccc ctgtctgcac ccggaggaaa ttgccaagag   1020
caggacttgg gactaaacgc acctcaatct gtgagaatgc ccttggaggc tgaaatggct   1080
gcacaaattc attacctggg cattgacaac gaggaaacta tcgcgcaaaa tcagccaaat   1140
tcctataagc gtctacgtgt ccccgcaggt ctggctatgg cgacgcctgc cgcggtttct   1200
acggcacaat cctctcattg taaagtctac gttgccccgc agcagtcatg cacctcgcct   1260
tctgatatga ctccgactct aaccgcatca gccttacatc tgccaccgca gggatctctt   1320
tgcccgttca tgacatcaaa tcctttagac gagctcatgc aaagcctgtc gcaggagaat   1380 cttcttcct cctgctcctc gacctctcca tctatcgcac ccgaagttga tgtacccagc    1440
atgcatgaca tactcatttg ggacctaaat gggaaacata gccgcccttc ttcccttagc   1500
tcctgggacg aggagggctt cgatggagtc tcaacctcat cttcccctgc aagcattgac   1560
aatcacgttg tttgccaacc tccggatttg agcgagcttc agtatgcgaa agctgcgtga   1620
```

```
<210> SEQ ID NO 17
<211> LENGTH: 399
<212> TYPE: DNA
<213> ORGANISM: Artificial Sequence
<220> FEATURE:
<223> OTHER INFORMATION: Blasticidin resistance gene codon optimized for
      Nannochloropsis

<400> SEQUENCE: 17
tcaaccctcc cagacgtagc cagagggaag caactccctg atgccaaccg ctgtgggctg      60
cccatcggaa tctttgacaa ttgccttgat ccccgggtgc aagtcaagca gcacctgccg     120
acatcgcccg cacggagaca gaatgccgcg gttttcgttc ccgatggcca ctatgcacgt     180
cagatttccg gcagcagccg cagcggccgt tccgaggacc acgagctccg cgcatggccc     240
tccggtgaaa tgatatacat tcacgccggt aaagatccga ccgtcggacg agagggctgc     300
actggccacc gagtagtcct cgctaatagg tatgctgttg atggtcgcag ttgcacgttc     360
gatcagcgtg gattcctctt gggataaagg cttggccat                            399

<210> SEQ ID NO 18
<211> LENGTH: 702
<212> TYPE: DNA
<213> ORGANISM: Artificial Sequence
<220> FEATURE:
<223> OTHER INFORMATION: Green Fluorescent Protein gene codon optimized
      for Nannochloropsis

<400> SEQUENCE: 18
atgttggaga gcgacgagag cggcctgccc gccatggaga tcgagtgccg catcaccggc      60
accctgaacg gcgtggagtt cgagctggtg ggcggcggag agggcacccc cgagcagggc     120
cgcatgacca acaagatgaa gagcaccaaa ggcgccctga ccttcagccc ctacctgctg     180
agccacgtga tgggctacgg cttctaccac ttcggcacct accccagcgg ctacgagaac     240
cccttcctgc acgccatcaa caacggcggc tacaccaaca cccgcatcga gaagtacgag     300
gacggcggcg tgctgcacgt gagcttcagc taccgctacg aggccggccg cgtgatcggc     360
gacttcaagg tgatgggcac cggcttcccc gaggacagcg tgatcttcac cgacaagatc     420
atccgcagca acgccaccgt ggagcacctg cacccccatgg gcgataacga tctggatggc     480
agcttcaccc gcaccttcag cctgcgcgac ggcggctact acagctccgt ggtggacagc     540
cacatgcact tcaagagcgc catccacccc agcatcctgc agaacggggg ccccatgttc     600
gccttccgcc gcgtggagga ggatcacagc aacaccgagc tgggcatcgt ggagtaccag     660
cacgccttca agaccccgga tgcagatgcc ggtgaagaat aa                        702

<210> SEQ ID NO 19
<211> LENGTH: 20
<212> TYPE: DNA
<213> ORGANISM: Primer JLC-good-MybTF-RT-F for Malta gene

<400> SEQUENCE: 19
tgtaaagtct acgttgcccc                                                  20

<210> SEQ ID NO 20
<211> LENGTH: 20
<212> TYPE: DNA
<213> ORGANISM: Primer JLC-good-MybTF-RT-F for Malta gene

<400> SEQUENCE: 20
tgtaaggctg atgcggttag                                                  20
```

```
<210> SEQ ID NO 21
<211> LENGTH: 849
<212> TYPE: DNA
<213> ORGANISM: Nannochloropsis gaditana

<400> SEQUENCE: 21
atgtcacggt cgcggtcctg ttccgaagct tctgcggcct cttcgtcatc ggcagcagca        60
gcgtcttcga ctcacgcccc ttcttcgcgc ggagcttcgg tggccgacgg tgctgcaagg       120
gagcgagaag ataatggcaa acgcctgagg tcaccgagcc ctgccggtgg tgaagcttct       180
ggttccgagg aagcggaaga ggatgatgag cccgccaaat tgcatgtttc tggtctaaca       240
agaaacgtga cagaggagca tctcaacgag atattcgcca catttgggaa gctgtcgcgt       300
gtggaactgg tacttgaccg acgagtgggc ttatcgcggg gcttcgccta tgttgagtac       360
gatcatcgga aggacgctga ggaagcccag ctgtacatgg acggtggtca gcttgacggc       420
gcacctttga aagtgaactt tgtgcttttg ggcggagccg cagccgatct cctgtatccc       480
gtggcggtgg tcgagaaagg gacctttacg atcgcaatgg cggtccgccg gagaggaggg       540 gcggggagc tcaatgggag gggcggcggg gccggtctcg ttctccgcct cgggggggtc       600
gacacgaccg aggtcggttg ccgccagggc ggtttactcg aggagagcgc ggacgcagcc       660 cccctaccg tcgccagcca gaccctcgcg gctggtcgcc gccacggcgc gggccgggtg       720
ggcgggcatc tccgcctcgg gccgcggtcg cagccggagc agccgctcct cacgcagccg       780
ttcctagatg gaggggggcgg cgccaacagg gaaggcaagc aggagtctca cccgccgctt       840
gaggcttga                                                               849

<210> SEQ ID NO 22
<211> LENGTH: 19
<212> TYPE: DNA
<213> ORGANISM: Primer JLC-RT-1704-F

<400> SEQUENCE: 22
gaggaagcgg aagaggatg                                                     19

<210> SEQ ID NO 23
<211> LENGTH: 19
<212> TYPE: DNA
<213> ORGANISM: Primer JLC-RT-1704-F

<400> SEQUENCE: 23
gaggaagcgg aagaggatg                                                     19
```

BIOMASS PRODUCTIVITY REGULATOR

CROSS-REFERENCE TO RELATED APPLICATION

This application claims benefit of priority under 35 U.S.C. §119(e) to U.S. Ser. No. 61/922,388 filed Dec. 31, 2013, the entire content of which is incorporated herein by reference in its entirety.

FIELD OF THE INVENTION

The present application relates generally to the field of molecular biology and genetics. Specifically, this application relates to methods and materials involved in genetically modifying microorganisms to improve productivity. This application further provides recombinant microorganisms such as microalgae having increased productivity.

INCORPORATION OF SEQUENCE LISTING

The material in the accompanying sequence listing is hereby incorporated by reference into this application. The accompanying sequence listing text file, named SGI1770_1_Sequence_Listing_ST25.txt, was created on Dec. 30, 2014 and is 29 kb. The file can be accessed using Microsoft Word on a computer that uses Windows OS.

BACKGROUND OF THE INVENTION

Microalgae have recently attracted considerable interest owing to numerous consumer products and applications that can be produced from these organisms. The microalgae-based product portfolio stretches from biomass production for food and animal feed to valuable products extracted from microalgal biomass, including lipids which can be converted into fuel molecules. Low biomass yields are identified as a key driver of the high cost of algal biofuels because of the high capital investment projected as necessary to achieve commercial-scale volumes of biofuel.

Transcription factors can modulate gene expression, either increasing or decreasing (inducing or repressing) the rate of transcription. This modulation results in differential levels of gene expression at various developmental stages, in different growth phases and cell types, and in response to different exogenous (e.g., environmental) and endogenous stimuli throughout the life cycle of the organism. Because transcription factors are key controlling elements of biological pathways, altering the expression levels of one or more transcription factors can change entire biological pathways in an organism.

SUMMARY OF THE INVENTION

The present application describes the discovery of gene sequences and polypeptides encoded thereby that, when overexpressed in microorganisms such as algae, confer increased productivity on the microorganisms.

In one aspect the present invention provides an isolated or recombinant nucleic acid molecule that encodes a polypeptides that includes an amino acid sequence having at least 65%, at least 70%, at least 75%, at least 80%, at least 85%, at least 90%, at least 95%, at least 96%, at least 97%, at least 98%, or at least 99% identity to the amino acid sequence of SEQ ID NO:2. In some examples, a polypeptide that includes an amino acid sequence having at least 65% identity to SEQ ID NO:2 has at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4. In some examples, the nucleic acid sequences have at least 50%, at least 55%, at least 65%, at least 70%, at least 75%, at least 80%, at least 85%, at least 90%, at least 95%, at least 96%, at least 97%, at least 98%, or at least 99% identity to the nucleotide sequence of SEQ ID NO:3 or SEQ ID NO:16. A polypeptide encoded by a nucleic acid molecule as provided herein can comprise, for example, a MYB-like transcription factor, e.g., a polypeptide that recruits to pfam PF00249. The amino acid sequence of the MYB-like transcription factor in some examples can comprise the amino acid domain of SEQ ID NO:2. The isolated or recombinant nucleic acid molecules can encode polypeptides with at least 50%, at least 55%, at least 60%, at least 65%, at least 70%, at least 75%, at least 80%, at least 85%, at least 90%, at least 95%, at least 96%, at least 97%, at least 98%, or at least 99% identity to a MYB-like polypeptide of a microbial species, such as, for example, a MYB-like polypeptide of a microalga or a heterokont species.

Also provided herein are isolated or recombinant nucleic acid molecules that include a nucleic acid sequence hybridizing under high stringency conditions to a nucleic acid sequence selected from the group consisting of SEQ ID NO:1 and SEQ ID NO:3; a complement of any thereof, or a fragment of either. Also provided herein are isolated or recombinant nucleic acid molecules that include a nucleic acid sequence having at least 65%, at least 70%, at least 75%, at least 80%, at least 85%, at least 90%, at least 95%, at least 96%, at least 97%, at least 98%, or at least 99% identity to a nucleic acid sequence selected from the group consisting of SEQ ID NO:1; SEQ ID NO:3; a fragment of either; or a complement of any thereof. Further provided herein are isolated or recombinant nucleic acid molecules that include a nucleic acid sequence encoding a polypeptide that comprises an amino acid sequence having at least 50%, at least 55%, at least 60%, at least 65%, at least 70%, at least 75%, at least 80%, at least 85%, at least 90%, at least 95%, at least 96%, at least 97%, at least 98%, or at least 99% identity to an amino acid sequence selected from the group consisting of SEQ ID NO:2, SEQ ID NO:4; and fragments of any thereof. Additionally provided herein are isolated or recombinant nucleic acid molecules including a nucleic acid sequence that is an antisense or interfering RNA to a nucleic acid sequence according any one of the preceding aspects and embodiments.

In various examples, the isolated or recombinant nucleic acid molecules provided herein can include one or more of the following features: The isolated or recombinant nucleic acid molecules can have nucleotide sequences that are different from (i.e., not 100% identical to) a nucleotide sequence of a naturally-occurring gene. The presently provided isolated or recombinant nucleic acid molecules can comprise a cDNA sequence. The presently provided isolated or recombinant nucleic acid molecules can comprise a vector. The provided isolated or recombinant nucleic acid molecules can comprise a heterologous regulatory element operably linked to a nucleic acid sequence as provided herein that encodes a polypeptide that includes a Myb domain. Further, an isolated or recombinant nucleic acid molecule as disclosed herein, when expressed in a host cell, can result in increased productivity of the host cell. For example, elevated expression of a nucleic acid molecule as disclosed herein in a microalgal or heterokont cell can result in higher productivity of the microalgal cell or heterokont cell when compared with a control cell that does not express the nucleic acid molecule. The higher productivity can be, for example, a higher growth rate, greater biomass productivity, or higher rate or level of production of a biomolecule such as, for example, a lipid, protein, polymer, pigment, or carbohydrate, including an alcohol.

In particular examples, provided herein are isolated or recombinant nucleic acid molecules that include a nucleic acid sequence encoding a polypeptide having at least 65%, at least 70%, at least 75%, at least 80%, at least 85%, at least 90%, at least 95%, at least 96%, at least 97%, at least 98%, or at least 99% identity to SEQ ID NO:4, or to a functional fragment of any thereof, in which the polypeptide includes a MYB-like DNA-binding domain having at least 65%, at least 70%, at least 75%, at least 80%, at least 85%, at least 90%, at least 95%, at least 96%, at least 97%, at least 98%, or at least 99% identity to SEQ ID NO:2.

Also provided herein is nucleic acid molecule having a nucleic acid sequence with at least about 30%, 35%, 40%, or 45% nucleotide sequence identity, and in some examples at least about 50%, at least about 55%, at least about 60%, at least about 65%, at least about 70%, at least about 75%, or at least about 80% sequence identity, for example at least about 85%, at least about 90%, at least about 95% or at least about 97% sequence identity to the nucleic acid sequence of SEQ ID NO:1. The nucleic acid molecule can encode a MALTA-like polypeptide, such as any disclosed herein, for example, a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to a MALTA-like polypeptide, including a microbial MALTA-like polypeptide, such as for example, to the polypeptide of SEQ ID NO:4.

Alternatively, a nucleic acid molecule as provided herein can comprise a sequence complementary to a sequence having at least 65%, for example, at least 85%, at least 90%, at least 95%, at least 96%, at least 97%, at least 98%, or at least 99% identity to SEQ ID NO:1 or a fragment thereof, for example a fragment of at least twenty, at least thirty, at least forty at least fifty or at least sixty nucleotides thereof, including a complement of a portion of any of the foregoing sequences that can be provided, for example, in an RNAi or antisense RNA construct. Further provided are isolated or recombinant nucleic acid molecules comprising nucleic acid sequences which are an interfering RNA to any of the nucleotide sequences provided herein.

A nucleic acid molecule as provided herein can be a fragment of the disclosed polynucleotides consisting of oligonucleotides of at least 12, at least 15, at least 20, at least 50, at least 100, at least 200, at least 500, or at least 1000 contiguous nucleotides, or up to the number of nucleotides present in a full-length MALTA-like protein-encoding nucleotide sequence disclosed herein.

Further included are nucleic acid molecules encoding variants of MALTA-like proteins, and recombinant MALTA-like polypeptides encoded by any of the recombinant nucleic molecules provided herein.

The invention also provides nucleic acid constructs comprising a nucleic acid sequence as provided herein operably linked to one or more sequences that can regulate or mediate transcription, translation, or integration of nucleotide sequences into a host genome. Further included are vectors that comprise a nucleic acid molecule as provided herein.

Further included herein is a nucleic acid molecule comprising a promoter sequence, where the promoter sequence includes a nucleotide sequence at least 90%, at least 95%, at least 96%, at least 97%, at least 98%, or at least 99% identical to at least 100, at least 200, at least 300, at least 400, at least 500, at least 600, at least 700, at least 800, at least 900, or 1000 contiguous nucleotides of SEQ ID NO:7, for example, to at least 95% identical to at least 100, at least 200, at least 300, at least 400, at least 500, at least 600, at least 700, at least 800, at least 900, or 1000 contiguous nucleotides from the 3' end of SEQ ID NO:7. The promoter sequence can comprise a a nucleotide sequence at least 90% or at least 95% identical to SEQ ID NO:7. The nucleic acid molecule can in some examples be a vector. Alternatively or in addition, the nucleic acid molecule can be a nucleic acid molecule in which the promoter sequence is operably linked to a nucleic acid sequence that is heterologous with respect to the promoter sequence. The heterologous sequence can be, for example, a nucleotide sequence encoding a polypeptide (that is not the 60S RPL24 polypeptide the promoter is operably linked to in the native organism from which it is derived) or a functional RNA such as an antisense RNA, RNAi construct, ribozyme, etc.

Further included herein is a nucleic acid molecule comprising a terminator sequence, where the terminator sequence includes a nucleotide sequence at least 90%, at least 95%, at least 96%, at least 97%, at least 98%, or at least 99% identical to SEQ ID NO:8. The nucleic acid molecule can in some examples be a vector. Alternatively or in addition, the nucleic acid molecule can be a nucleic acid molecule in which the promoter sequence is operably linked to a nucleic acid sequence that is heterologous with respect to the terminator sequence. The heterologous sequence can be, for example, a nucleotide sequence encoding a polypeptide or a functional RNA such as an antisense RNA, RNAi construct, ribozyme, etc.

Another aspect of the invention is a recombinant microorganism that includes a non-native nucleic acid molecule encoding a polypeptide that includes an amino acid sequence having at least 65%, at least 70%, at least 75%, at least 80%, at least 85%, at least 90%, at least 95%, at least 96%, at least 97%, at least 98%, or at least 99% identity to a MYB-like DNA-binding domain of SEQ ID NO:2. The polypeptide encoded by the non-native nucleic acid molecule is preferably a MYB-like transcription factor, such as a polypeptide having at least 50% identity to a naturally-occurring MYB-like transcription factor of a plant or microorganism, e.g., an alga or heterokont. In various examples, the recombinant microorganism includes a non-native gene encoding a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence of SEQ ID NO:4. The recombinant microorganism cell or plant cell that includes a non-native gene encoding a polypeptide having a MYB-like DNA-binding domain-homologous sequence as disclosed herein can exhibit higher productivity than is exhibited by a control cell substantially identical to the recombinant microorganism cell or plant cell, with the exception that the control cell does not include a non-native gene encoding a polypeptide having a MYB-like DNA-binding domain sequence. For example, expression of the non-native gene in an algal or heterokont cell can result in the algal or heterokont cell producing a greater amount of biomass or a greater amount of one or more biomolecules, such as, without limitation, a lipid, a polymer, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a pigment or colorant.

A recombinant microorganism having a non-native gene encoding a polypeptide having a MYB-like DNA-binding domain of the invention can comprise, e.g., any of the nucleic acid molecules comprising a nucleic acid sequence that encodes a polypeptide including a MYB-like DNA-binding domain described herein. The nucleic acid sequence can encode a polypeptide that is heterologous (of a different species) with respect to the recombinant host cell or organism or homologous (of the same species) with respect to the recombinant host cell or organism. In some examples, the nucleic acid molecule can encode a variant of a naturally-occurring polypeptide that may be either homologous or heterologous with respect to the host cell or organism.

A host cell that includes a non-native gene as provided herein that encodes a MYB-like polypeptide, homolog, or variant can further include one or more additional non-native genes that may confer any trait or interest, such as, but not limited to, production of biomolecules of interest, such as one or more proteins, pigments, alcohols, or lipids.

Suitable host cells to be modified using the materials and methods according to the present invention include, but are not limited to, algal cells, heterokont cells, fungal cells, insect cells, mammalian cells, and plant cells. Particularly suitable host cells are bacteria, protists, microalgae, phytoplankton, heterokonts, fungi, and protozoa. Heterokont species considered for use in the invention include, but are not limited to, *Bacillariophytes, Eustigmatophytes, Labrinthulids*, and *Thraustochytrids*, such as, for example, species of *Labryinthula, Labryinthuloides, Thraustochytrium, Schizochytrium, Aplanochytrium, Aurantiochytrium, Oblongichytrium, Japonochytrium, Diplophrys*, or *Ulkenia*.

Algal species suitable for the method of the invention include microalgae such as, for example, species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phœodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. Non-limiting examples of particularly suitable species include, for instance, diatoms such as, for example, a species of any of the genera *Amphora, Chaetoceros, Cyclotella, Fragilaria, Fragilaropsis, Navicula, Nitzschia, Phœodactylum*, or *Thalassiosira*, or eustigmatophytes, e.g., *Eustigmatos, Monodus, Nannochloropsis*, or *Vischeria*.

A microorganism that includes a non-native gene encoding a polypeptide having a MYB-like DNA-binding domain as provided herein can have improved productivity when compared with a control microorganism that does not include the non-native gene encoding a MYB-like DNA-binding domain-containing polypeptide. Higher productivity can be demonstrated, for example, by measuring growth rates (for example, by cell counts or optical density of a culture) or total organic carbon (TOC) or ash free dry weight accumulation, or by quantitating any of various biomolecules produced by the recombinant microorganism (such as for example, one or more lipids, polymers, proteins, pigments, carbohydrates, etc.).

Also provided herein are methods for modulating a growth characteristic of a host cell. Such methods comprise introducing into the host cell a nucleic acid molecule according to any one of preceding aspects and embodiments of the invention, wherein the nucleic acid molecule confers a modulated growth characteristic of the host cell as compared to a control cell that does not contain the nucleic acid molecule of the invention. In some examples, the modulated growth characteristic can be higher biomass productivity.

Also provided herein are methods of producing biomass or at least one bioproduct by culturing recombinant host cells having a modulated growth characteristic, such as the recombinant host cells disclosed herein. The methods include culturing a recombinant host cell as disclosed herein that includes a non-native gene encoding a MYB-like protein, such as a nucleic acid molecule as disclosed herein that encodes a MYB-like protein, in a suitable growth medium to produce a culture of recombinant cells, and recovering biomass or at least one bioproduct from the culture. The method can optionally include inducing expression of the non-native gene that encodes the MYB-like protein. The microorganism in some examples can be an alga such as, for example, a microalga. The cell culture can be a photoautotrophic culture. Non-limiting examples of products that can be made using the methods of the invention include food, feed, biofuel, bio-chemical, pharmaceutical, or medicinal products. In some examples, exemplary products that can be made using the methods of the invention include biomass, lipids, polyketides, terpenoids, pigments, antioxidants, vitamins, nucleotides, nucleic acids, amino acids, peptides, proteins, carbohydrates, alcohols, hormones, cytokines, or a polymers. Exemplary lipids that can be made using the methods of the invention include fatty acids, fatty alcohols, fatty aldehydes, fatty acid esters, wax esters, hydrocarbons, triacylglycerides, diacylglycerides, monoacylglycerides, phospholipids, and terpenoids. The methods can include isolating the product from the culture.

A further aspect of the invention provides isolated or recombinant polypeptides. The polypeptides are encoded by nucleic acid molecules having nucleic acid sequences according to anyone of the preceding aspects and embodiments. Thus, compositions that include at least one isolated or recombinant polypeptide of the invention are also within the scope of the present application.

These and other objects and features of the invention will become more fully apparent from the following detailed description of the invention and the claims.

BRIEF DESCRIPTION OF THE DRAWINGS

FIG. 1A provides a graph demonstrating fatty acid methyl ester (FAME) production (GE-5385 and GE-5386 dashed lines are coincident); FIG. 1B provides a graph demonstrating total organic carbon (TOC) accumulation; and FIG. 1C depicts FAME/TOC ratios of *Nannochloropsis* cells overexpressing MALTA compared to wild-type control WE-03730. In each case, the two lines that outperformed wild-type are shown as dashed lines (Myb-1, GE-5385 and Myb-2, GE-5386) while the remaining transgenic lines (Myb-3 to -10) are shown as solid gray lines. The black solid lines depict the performance of wild-type cells, marked on the graph.

DETAILED DESCRIPTION OF THE INVENTION

Figure 1:
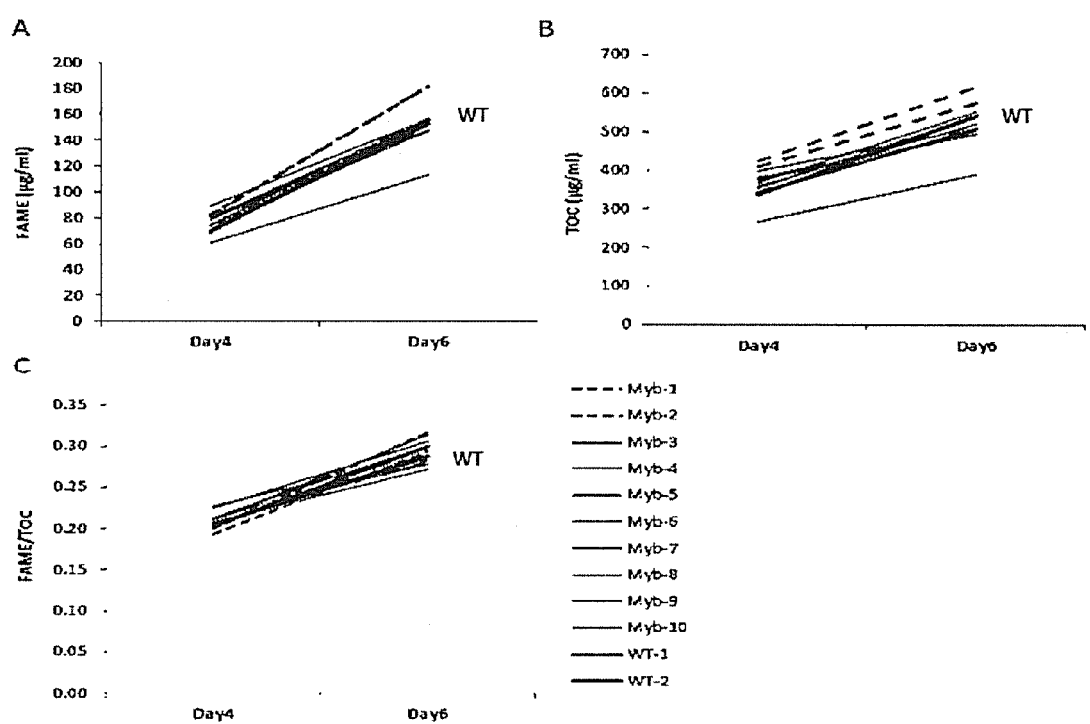
FIGS. 1A, 1B, and 1C illustrate the results of experiments assessing productivity level of ten transgenic lines transformed with an overexpression construct for the *Nannochloropsis* MALTA gene Myb-5256 in a constant light productivity assay.

The present application relates to compositions, methods and related materials for modifying characteristics of microorganisms, particularly those associated with improved productivity. In various aspects, the application discloses recombinant microorganisms, such as microalgae and heterokonts that express a non-native gene encoding a regulatory protein that affects productivity, such as, for example, biomass productivity.

Throughout this disclosure, various information sources are referred to and/or incorporated by reference. The information sources include, for example, scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted.

Headings within the application are solely for the convenience of the reader, and do not limit in any way the scope of the invention or its embodiments.

Some Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", and "A and B".

"About" means plus or minus 10% of the provided value. Where ranges are provided, they are inclusive of the boundary values.

As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that function in a manner similar to a naturally-occurring amino acid.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As non-limiting examples, an attenuated gene may be a mutated or disrupted gene (e.g., a gene disrupted by partial or total deletion, or insertional mutation) or having decreased expression due to alteration of gene regulatory sequences.

"Biofuels", as used herein, refer to renewable energy sources from living organisms, such as higher plants, fungi, algae, or microorganisms. As such, biofuels can be solid, liquid or gaseous fuels derived from algal, fungal, microbial or plant materials, biomass, sugars or starches, such as ethanol or biodiesel derived from vegetable oils or algal oil, and the like. A biofuel is a fuel in its own right, but may be blended with petroleum-based fuels to generate a finished fuel. A biofuel may be used as a replacement for petrochemically-derived gasoline, diesel fuel, or jet fuel.

A "cDNA" is a DNA molecule that comprises at least a portion of the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred examples, a cDNA does not include one or more intron sequences that occur in the naturally-occurring gene (in the genome of an organism) that the cDNA corresponds to. For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene, but are separated by an intron). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences and/or compiled from the sequences of multiple partial cDNAs.

A "control organism", "control microorganism", or "control cell" as used in the present invention provides a reference point for measuring changes in phenotype of the subject organism, microorganism, or cell. A control organism, microorganism, or cell may comprise, for example, (a) a wild-type organism, microorganism, or cell, i.e., of the same genotype as the starting material for the genetic alteration which resulted in the subject organism, microorganism, or cell; (b) an organism or cell of the same genotype as the starting material but which has been transformed with a null construct (i.e. a construct which has no known effect on the trait of interest, such as a construct lacking a gene encoding the polypeptide of interest, e.g., lacking a gene encoding a MALTA-like polypeptide); (c) an organism or cell which is a non-transformed segregant among progeny of a subject organism or cell; or (d) the subject organism, microorganism, or cell itself, under conditions in which the gene of interest is not expressed. In some instances, "control organism" may in some cases refer to an organism that does not contain the exogenous nucleic acid present in the transgenic organism of interest, but otherwise has the same or similar genetic background as such a transgenic organism.

"Domains" are groups of substantially contiguous amino acids in a polypeptide that can be used to characterize protein families and/or parts of proteins. Such domains may have a "fingerprint", "motif", or "signature" that can comprise conserved primary sequence, secondary structure, and/or three-dimensional conformation. Generally, domains are correlated with specific in vitro and/or in vivo activities. A domain can be of any size, by way of example, a domain may have a length of from 4 amino acids to about 400 amino acids, e.g., from 4 to about 50 amino acids, or 4 to about 20 amino acids, or 4 to about 10 amino acids, or about 25 to about 100 amino acids, or about 35 to about 65 amino acids, or about 50 to about 100 amino acids, or about 75 to 120 amino acids, or about 200 to about 300 amino acids, or about 300 to about 400 amino acids.

"Down-regulation" refers to regulation that decreases production of expression products (mRNA, polypeptide, biological activity, or combinations of any thereof) relative to basal or native states.

The term "endogenous," within the context of the present disclosure refers to any polynucleotide, polypeptide or protein sequence which is a natural part of a cell.

"Exogenous" with respect to a nucleic acid or gene indicates that the nucleic or gene has been introduced ("transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. An exogenous nucleic acid can also be a sequence that is homologous to an organism (i.e., the nucleic acid sequence occurs naturally in that species or encodes a polypeptide that occurs naturally in the host species) that has been reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. A nucleic acid is considered exogenous if it has been introduced into a progenitor of the cell, organism, or strain under consideration.

As used herein, "expression" refers to the process of converting genetic information of a polynucleotide into RNA through transcription, which is typically catalyzed by an enzyme, RNA polymerase, and, where the RNA encodes a polypeptide, into protein, through translation of mRNA on ribosomes to produce the encoded protein "Fragment", with respect to a polynucleotide, refers to a clone or any part of a polynucleotide molecule, particularly a part of a polynucleotide that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, for example at least about 30 nucleotides or at least about 50 nucleotides of any of the sequences provided herein. Exemplary polynucleotide fragments are the first sixty consecutive nucleotides of the polynucleotides listed in the Sequence Listing. Exemplary fragments also include fragments that comprise a region that encodes a conserved B domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, for example at least about 20 amino acid residues in length, for example at least about 30 amino acid residues in length.

The term "functional homolog" as used herein describes those molecules that have sequence similarity and also share at least one functional characteristic such as a biochemical activity. Functional homologs will typically give rise to the same characteristics to a similar, but not necessarily the same, degree. Functionally homologous proteins give the same characteristics where the quantitative measurement produced by one homolog is at least 10% of the other; more typically, at least 20%, between about 30% and about 40%; for example, between about 50% and about 60%; between about 70% and about 80%; or between about 90% and about 95%; between about 98% and about 100%, or greater than 100% of that produced by the original molecule. Thus, where the molecule has enzymatic activity the functional homolog will have the above-recited percent enzymatic activities compared to the original enzyme. Where the molecule is a DNA-binding molecule (e.g., a polypeptide) the homolog will have the above-recited percentage of binding affinity as measured by weight of bound molecule compared to the original molecule.

A functional homolog and the reference polypeptide may be naturally occurring polypeptides, and the sequence similarity may be due to convergent or divergent evolutionary events. Functional homologs are sometimes referred to as orthologs, where "ortholog", refers to a homologous gene or protein that is the functional equivalent of the referenced gene or protein in another species.

Variants of a naturally-occurring functional homolog, such as polypeptides encoded by mutants or a wild-type coding sequence, may themselves be functional homologs. As used herein, functional homologs can also be created via site-directed mutagenesis of the coding sequence for a productivity-modulating polypeptide, for example a MALTA-like polypeptide, or by combining domains from the coding sequences for different naturally-occurring MALTA-like polypeptides. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass-modulating polypeptides. Sequence analysis can involve BLAST, Reciprocal BLAST, or PSI-BLAST analysis of non-redundant databases using amino acid sequence of a biomass-modulating polypeptide as the reference sequence. Amino acid sequence is, in some instances, deduced from the nucleotide sequence. Typically, those polypeptides in the database that have greater than 40% sequence identity are candidates for further evaluation for suitability as a biomass-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in productivity-modulating polypeptides, e.g., conserved functional domains. As used herein a "MALTA-like polypeptide" is a polypeptide that belongs to pfam PF00249 (MYB-like DNA-binding domain containing proteins) as provided herein and depicted, for example, in the amino acid sequence of SEQ ID NO:2 or amino acid residues 52-97 of SEQ ID NO:4 of the Sequence Listing. This Pfam family has been reported previously to include a diverse range of mostly DNA-binding domains that contain a helix-turn-helix motif, including DNA-binding domains from MYB-like proteins, as well as those of the SAINT domain family (Aasland et al., *Trends Biochem. Sci.* 21:87-88, 1996).

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., is from a different species with respect to the host cell. For example, a transgenic *Nannochloropsis* microorganism transformed with the coding sequence for a fatty acid desaturase from a *Tetraselmis* microorganism or from a plant is transformed with a heterologous desaturase gene. When referring to nucleic acid sequences operably linked or otherwise joined to one another in a nucleic acid construct or molecule, "heterologous sequences", as used herein, are those that are not operably linked or are not contiguous to each other in nature. For example, a promoter from *Tetraselmis* sp. is considered heterologous to a *Nannochloropsis* coding region sequence. Also, a promoter from a gene encoding a sugar transporter gene from *Nannochloropsis* is considered heterologous to a sequence encoding a *Nannochloropsis* fatty acid desaturase. Similarly, when referring to a gene regulatory sequence or to an auxiliary nucleic acid sequence used for maintaining or manipulating a gene sequence (e.g., a promoter, enhancer, 5' untranslated region, 3' untranslated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source (e.g., different gene, whether from the same or different species as the host organisms) than the gene with which the regulatory or auxiliary nucleic acid sequence is juxtaposed in a construct, genome, chromosome, or episome. When referring to a protein functional domain, such as a cellular localization sequence or a receptor binding site, "heterologous" can also mean that the protein functional domain is from a different source (e.g., protein) than the rest of the protein region with which it is juxtaposed in an engineered protein. Similarly, when referring to a promoter sequence of an engineered gene, "heterologous" means that the promoter is derived from a different gene than that to which it is linked by genetic engineering.

When used in reference to a polynucleotide, a gene, a nucleic acid, a polypeptide, or an enzyme, the term "homologous" refers to a polynucleotide, gene, a nucleic acid, polypeptide, or an enzyme derived from the host species, e.g., is from the same species with respect to the host cell, regardless of whether the homologous polynucleotide, gene, nucleic acid, polypeptide, or enzyme has been introduced into the host cell (exogenous) or is endogenous with respect to the host cell.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The term "mis-expression" refers to an increase or decrease in the transcription of a coding region into a complementary RNA sequence as compared to the parental wild-type, for example, alga or plant. This term also encompasses expression of a gene or coding region for a different time period as compared to the wild-type and/or from a non-natural location within the parental genome. The term "overexpression" or "increased expression" as used herein refers to a greater expression level of a gene, a polynucleotide sequence, or a polypeptide, in a host cell compared to a wild-type cell or a wild-type organism, at any developmental or temporal stage. Methods for increasing expression of genes or gene products are well documented in the art and include, for example, overexpression driven by appropriate promoters (e.g. constitutive promoters), the use of transcription enhancers or translation enhancers. Overexpression may also under control of an inducible or a growth-phase specific promoter. For example, overexpression may occur throughout an algal cell, in specific growth phases of the alga, or in the presence or absence of particular environmental signals, depending on the promoter used.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest.

"Percentage of sequence identity," as used herein, is determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base or amino acid residue occurs in both sequences to yield the number of matched positions, dividing the number of matched positions by the total number of positions in the window of comparison and multiplying the result by 100. Unless otherwise indicated, percent identity to a given sequence (SEQ ID NO) is used herein to refer to percent identity over the entire referenced sequence. That is, the referenced sequence or any specified segment thereof is the comparison window. Optimal alignment of sequences for comparison may be conducted by the local homology algorithm of Smith and Waterman (*Add. APL. Math.* 2:482, 1981), by the global homology alignment algorithm of Needleman and Wunsch (*J. Mol. Biol.* 48:443, 1970), by the search for similarity method of Pearson and Lipman (*Proc. Natl. Acad. Sci.* USA 85: 2444, 1988), by heuristic implementations of these algorithms (NCBI BLAST, WU-BLAST, BLAT, SIM, BLASTZ), or by inspection. GAP and BESIFIT, for example, can be employed to determine their optimal alignment of two sequences that have been identified for comparison. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, for example, at least 70%, at least 80%, at least 85%, at least 90%, at least 95%, or at least 96%, 97%, 98% or 99% sequence identity compared to a reference sequence using the programs. In addition, pairwise sequence homology or sequence similarity, as used refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Query nucleic acid and amino acid sequences were searched against subject nucleic acid or amino acid sequences residing in public or proprietary databases. Such searches were done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Typically the following parameters for NCBI BLAST were used: Filter options were set to "default", the Comparison Matrix was set to "BLOSUM62", the Gap Costs were set to "Existence: 11, Extension: 1", the Word Size was set to 3, the Expect (E threshold) was set to 1e-3, and the minimum length of the local alignment was set to 50% of the query sequence length. Sequence identity and similarity may also be determined using GENOMEQUEST™ software (Gene-IT, Worcester, Mass. USA).

A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or, in the case of peptidomimetics, other bonds such as, for example, ester or ether bonds. Full-length polypeptides, truncated polypeptides, point mutants, insertion mutants, splice variants, chimeric proteins, and fragments thereof are encompassed by this definition. As used herein, the expression "substantially conserved amino acid sequences" refers to regions of amino acid homology between polypeptides of the same type or family from different sources. One skilled in the art could align the amino acid sequences of MALTA-like polypeptides from different sources to identify the segments therein which are the substantially conserved amino acid sequences. The skilled person could then determine whether the identified segments have the characteristics disclosed and claimed in the present invention.

As used herein "progeny" means a descendant, offspring, or derivative of an organism. For example, daughter cells from a transgenic alga are progeny of the transgenic alga. Because certain modifications may occur in succeeding generations due to mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence.

The term "recombinant protein" as used herein refers to a protein produced by genetic engineering, for example, by expression of a genetically engineered nucleic acid molecule in a cell.

The term "regulatory region" "regulatory sequence", "regulatory element", or "regulatory element sequence", as used in the present invention, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, "transgenic organism" refers to an organism which comprises a heterologous polynucleotide. When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, zinc finger nucleases, TALENs, or Crisper nucleases. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity to the reference polypeptide or polynucleotide. In other embodiments the variant can have at least 80%, at least 95%, at least 90% or at least 95%, at least 97%, at least 98%, or at least 99% sequence identity to the reference polypeptide or polynucleotide. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation. phosphorylation, etc.).

As used herein, "vector" refers to a nucleic acid molecule that includes at least one of a selectable marker gene or an origin of replication or autonomous replication sequence (ARS) that allows the vector to be replicated in a host cell, and in some examples includes both a selectable marker gene and at least one origin of replication or ARS. A vector in various examples includes one or more expression sequences and/or can include at least one sequence for mediating recombination.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein; this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

Polynucleotides and Polypeptides of the Invention

In one aspect of the present invention, the disclosure provides isolated or recombinant nucleic acid molecules, nucleic acid molecules that interfere with these nucleic acid molecules, and nucleic acid molecules that hybridize to these nucleic acid molecules. Additional aspects of the present application include the polypeptides encoded by the isolated or recombinant nucleic acid molecules of the present invention.

An isolated or recombinant nucleic acid molecule as provided herein can have a nucleic acid sequence that encodes a polypeptide having an amino acid sequence with at least 65%, at least 70%, at least 75%, at least 80%, at least 85%, at least 90%, at least 95%, at least 96%, at least 97%, at least 98%, or at least 99% identity to SEQ ID NO:4. Alternatively or in addition, an isolated or recombinant nucleic acid molecule as provided herein can have a nucleic acid sequence that encodes a polypeptide having an amino acid sequence with at least 65%, at least 70%, at least 75%, at least 80%, at least 85%, at least 90%, at least 95%, at least 96%, at least 97%, at least 98%, or at least 99% identity to SEQ ID NO:2. The encoded polypeptide can comprise, for example, a MALTA-like polypeptide. The MALTA-like polypeptide in some examples can have an amino acid sequence having at least 65%, at least 70%, at least 75%, at least 80%, at least 85%, at least 90%, at least 95%, at least 96%, at least 97%, at least 98%, or at least 99% identity to SEQ ID NO:4 (e.g., to the entire sequence of SEQ ID NO:4) or can comprise the amino acid sequence of SEQ ID NO:4, and can further comprise a MYB-like domain having at least 65%, at least 70%, at least 75%, at least 80%, at least 85%, at least 90%, at least 95%, at least 96%, at least 97%, at least 98%, or at least 99% identity to SEQ ID NO:2.

In some examples, an isolated or recombinant nucleic acid molecule as provided herein that encodes a polypeptide having at least 65%, at least 70%, at least 75%, at least 80%, at least 85%, at least 90%, at least 95%, at least 96%, at least 97%, at least 98%, or at least 99% identity to the polypeptide of SEQ ID NO:4 can be a genomic DNA. For example, a nucleic acid molecule as provided herein can be at least 75%, at least 80%, at least 85%, at least 90%, at least 95%, at least 96%, at least 97%, at least 98%, or at least 99% identical to SEQ ID NO:16.

A MYB-like domain containing polypeptide can be identified by the sequence characteristics of a MYB-like DNA-binding domain, i.e. Pfam ID PF00249, as provided herein and exemplified, for example, in the amino acid sequence of SEQ ID NO:2 or amino acid residues 52-97 of SEQ ID NO:4 of the Sequence Listing. This Pfam family has been reported previously to include a diverse range of mostly DNA-binding domains that contain a helix-turn-helix motif, including DNA-binding domains from MYB-like proteins, as well as those of the SANT domain family (Aasland et al., *Trends Biochem. Sci.* 21:87-88, 1996). For example, an amino acid sequence can be searched against the pfam database (e.g., at pfam.xfam.org or at janelia.org) to determine whether the amino acid sequence includes the myb-DNA-binding domain (PF00249) or whether a polypeptide that includes the amino acid sequence recruits to pfam PF00249 by having a bit score higher than the gathering cutoff of 24.4 for this family, preferably with an e-value of 0.1 or less.

An isolated or recombinant nucleic acid molecule as provided herein can encode a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to a naturally-occurring MYB-like domain containing polypeptide of a plant or microbial species, such as, for example, a MYB-like domain containing polypeptide of a plant, a microalga, or a heterokont species. Alternatively or in addition, the nucleic acid sequence can encode a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:2 or SEQ ID NO:4.

In some examples, the isolated or recombinant nucleic acid molecule includes a nucleic acid sequence encoding a polypeptide that comprises a MYB-like domain having an amino acid sequence with at least 85%, at least 90%, at least 95%, at least 96%, at least 97%, at least 98%, or at least 99% identity to SEQ ID NO:2. The MYB-like domain containing polypeptide can be a MALTA-like polypeptide. A MALTA-like polypeptide can in some examples comprise an amino acid sequence with at least 85%, at least 90%, at least 95%, at least 96%, at least 97%, at least 98%, or at least 99% identity to SEQ ID NO:4.

In further examples, provided herein are isolated or recombinant nucleic acid molecules that include a nucleic acid sequence encoding a polypeptide, such as a MALTA-like polypeptide, having at least 65%, at least 70%, at least 75%, at least 80%, at least 85%, at least 90%, at least 95%, at least 96%, at least 97%, at least 98%, or at least 99% identity to SEQ ID NO:4, in which the polypeptide includes a MYB-like domain having at least 85%, at least 90%, at least 95%, at least 96%, at least 97%, at least 98%, or at least 99% identity to SEQ ID NO:2.

At the nucleotide level, a nucleic acid molecule as provided herein can in some examples share at least about 30%, 35%, 40%, or 45% nucleotide sequence identity, and in some examples at least about 50%, at least about 55%, at least about 60%, at least about 65%, at least about 70%, at least about 75%, or at least about 80% sequence identity, for example at least about 85%, at least about 90%, at least about 95% or at least about 97% sequence identity, to one or more of SEQ ID NO:1, SEQ ID NO:3, and a region or fragment of any thereof. For example, a nucleic acid molecule as provided herein can in some examples have at least 50%, at least 55%, at least 60%, at least 65%, at least 70%, at least 75%, or at least 80% sequence identity, for example at least 85%, at least 90%, at least 95%, or at least 97% sequence identity to one or more of SEQ ID NO:1 and SEQ ID NO:3. In further examples, a nucleic acid molecule as provided herein can have at least 85%, at least 90%, at least 95%, or at least 97% sequence identity to one or more of SEQ ID NO:1, SEQ ID NO:3, or a complement of any thereof, including a complement of a portion of any of the foregoing sequences that can be provided, for example, in an RNAi or antisense RNA construct.

In various examples, the nucleic acid molecules disclosed herein comprise a nucleic acid sequence that encodes a MALTA-like polypeptide, that has at least 65% sequence identity to a naturally-occurring polypeptide of an algal or heterokont species, for example, at least 85% sequence identity to a naturally-occurring polypeptide of an algal or heterokont species.

An isolated or recombinant nucleic acid molecule as provided herein can in some examples have a nucleotide sequence that is different from (i.e., not 100% identical to) a nucleotide sequence of a naturally-occurring gene and/or the isolated or recombinant nucleic acid molecule comprise a cDNA sequence. For example, the isolated or recombinant nucleic acid molecules can have nucleotide sequences that are at least 65% identical to a naturally-occurring sequence, at least 85% identical to a naturally-occurring sequence, or between 95% and 99.9% identical to the sequence of a naturally-occurring gene. Alternatively or in addition, in some examples an isolated or recombinant nucleic acid molecule as provided herein can include a protein-encoding region that lacks one or more intervening non-coding sequences (introns) that are found in the genome of the organism that includes the gene, and can include two or more protein-encoding sequences of the gene that are continuous, where the two or more sequences are separated by introns in the unaltered genome of an organism. For example, the nucleic acid molecule can comprise a cDNA sequence, in which the cDNA sequence comprises a different sequence than is found in the genome of a naturally-occurring organism. Alternatively or in addition, the nucleic acid molecule can comprise a protein-encoding gene that includes a 5' untranslated region that is not contiguous with the protein-encoding portion of the nucleic acid molecule in the genome of a non-genetically modified organism. Alternatively or in addition to any of the above, the nucleic acid molecule can have a sequence that has one or more nucleobase changes with respect to the sequence of a naturally-occurring gene in the genome of an organism. For example, the nucleic acid molecule can have a sequence that has one or more nucleobase substitutions, deletions, or additions with respect to the sequence of a naturally-occurring gene in the genome of an organism.

Additionally, an isolated or recombinant nucleic acid molecule as provided herein, when expressed in a microbial host cell, can confer higher productivity on the microbial host cell. In some examples, expression of a nucleic acid molecule as disclosed herein in a microalgal or heterokont cell can result in the microalgal or heterokont cell having higher productivity when compared with a control cell that does not express the nucleic acid molecule, for example, the microbial host cell can demonstrate a higher growth rate, greater biomass productivity, or higher rate or level of production of a biomolecule such as, for example, a lipid, protein, pigment, or carbohydrate, including an alcohol. For example, the host cell can exhibit higher productivity with respect to a control cell of one or more products the host cell is engineered to synthesize.

An isolated nucleic acid molecule of the present invention can be produced using recombinant DNA technology (e.g., any or a combination of any of reverse transcription, restriction, ligation, polymerase reactions, including polymerase chain reaction (PCR) amplification, cloning, in vitro or in vivo recombination, etc.) or chemical synthesis. Isolated nucleic acid molecules include natural nucleic acid molecules and homologs thereof, including, but not limited to, natural allelic variants and modified nucleic acid molecules in which nucleotides have been inserted, deleted, and/or substituted, in such a manner that such modifications provide the desired effect on the biological activity of CCAAT-box binding factors as described herein.

A nucleic acid molecule variant can be produced using a number of methods known to those skilled in the art (see, for example, Sambrook et al. *Molecular Cloning: A Laboratory Manual.* 2nd ed. N.Y., Cold Spring Harbor Laboratory, Cold Spring Harbor Laboratory Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules, and combinations thereof. Nucleic acid molecule homologs can be selected from a mixture of modified nucleic acids by screening for the function of the protein encoded by the nucleic acid and/or by hybridization with a wild-type gene.

According to some embodiments of the present application, nucleic acid molecules of the present invention will include those nucleic acid molecules that specifically hybridize to one or more of SEQ ID NO:1, SEQ ID NO:3, fragments of any thereof, complements thereof and their fragments, under moderate or high stringency conditions. In particular examples, nucleic acid molecules of the present invention can comprise a nucleic acid sequence that hybridizes, under high stringency conditions, to a nucleic acid sequence selected from the group consisting of SEQ ID NO:1, SEQ ID NO:3, a complement thereof, or a fragment of either.

As used herein, two nucleic acid molecules are said to be capable of specifically hybridizing to one another if the two molecules are capable of forming an anti-parallel, double-stranded nucleic acid structure. Two molecules are said to be minimally complementary if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions. A nucleic acid molecule is said to be the complement of another nucleic acid molecule if they exhibit complete complementarity. As used herein, molecules are said to exhibit complete complementarity when every nucleotide of one of the molecules is complementary to a nucleotide of the other. Departures from complete complementarity are permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Conventional stringency conditions are described by Sambrook et al., supra, and by Haymes et al. In: *Nucleic Acid Hybridization, A Practical Approach*, IRL Press, Washington, D.C. (1985). For example, appropriate stringency conditions which promote DNA hybridization include, for example, 6.0× sodium chloride/sodium citrate (SSC) at about 45° C., followed by a wash of 2.0×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These and other conditions are known to those skilled in the art, or can be found in *Current Protocols in Molecular Biology*, John Wiley & Sons, N.Y. (1989), 6.3.1-6.3.6. Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70×C for several hours to overnight. High stringency conditions are preferably provided by 6×SSC, 5×Denhardt's solution, 100 mg/mL fish sperm DNA, and 0.1% (w/v) SDS, with incubation at 55° C. for several hours. Hybridization is generally followed by several wash steps. The wash compositions generally comprise 0.5× to about 10×SSC, and 0.01% (w/v) to about 0.5% (w/v) SDS with a 15 min incubation at about 20° C. to about 70° C. Preferably, the nucleic acid segments remain hybridized after washing at least one time in 0.1×SSC at 65° C.

A subset of the nucleic acid molecules of this invention includes fragments of the presently disclosed polynucleotides consisting of oligonucleotides of at least 12, at least 15, for example at least 16 or 17, or for example at least 18 or 19, such as at least 20 or more, consecutive nucleotides. Such oligonucleotides are fragments of the larger molecules having a sequence selected from the polynucleotide sequences in the Sequence Listing, and find use, for example, as interfering molecules, probes and primers for detection of the polynucleotides of the present invention.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule useful in the present invention, or of a size sufficient to encode an amino acid sequence having a biological activity of at least one domain of a polypeptide according to the present invention, e.g. MALTA-like proteins or other MYB-like domain containing proteins disclosed herein. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of a MALTA-like polypeptide or a MYB-like domain containing polypeptide, an entire MALTA-like polypeptide or MYB-like domain containing polypeptide, or several domains within an open reading frame encoding a MALTA-like or a MYB-like domain containing polypeptide.

The present invention provides, in various examples, nucleotide sequences comprising regions that encode polypeptides that may be the complete protein encoded by the gene represented by the polynucleotide, or may be fragments of the encoded protein. For example, polynucleotides provided herein can encode polypeptides constituting a substantial portion of the complete protein, for example, constituting a sufficient portion of the complete protein to provide the relevant biological activity, e.g., the activity of a MALTA-like polypeptide or MYB-like domain containing polypeptide. Of particular interest are polynucleotides of the present invention that encode a MALTA-like polypeptide. Such polynucleotides may be expressed in transgenic cells or transgenic organisms to produce cells and organisms having higher productivity, for example, higher biomass productivity.

Nucleic acid molecules that are fragments of these MALTA- or MYB-like protein-encoding nucleotide sequences are also encompassed by the present invention. A "MALTA fragment" or "MYB-like protein fragment", as used herein, is intended to be a portion of the nucleotide sequence encoding a MALTA or MYB-like domain containing protein. A fragment of a nucleotide sequence may encode a biologically active portion of a MALTA- or MYB-like domain containing polypeptide, or it may be a fragment that can be used as a hybridization probe or PCR primer using methods disclosed below. Nucleic acid molecules that are fragments of a MALTA-like nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length MALTA- or MYB-like domain protein-encoding nucleotide sequence disclosed herein (e.g., SEQ ID NO:3) depending upon the intended use. In some examples, a MALTA or MYB-like protein fragment encoded by a nucleic acid sequence as provided herein may have an N-terminal or a C-terminal truncation of at least about 100 amino acids, about 120, about 130, about 140, about 150, or about 160 amino acids relative to SEQ ID NO:4.

Fragments of the nucleotide sequences of the present invention include those that encode protein fragments that retain the biological activity of a MALTA-like or a MYB-like protein. By "retains activity" is intended that the fragment will have at least about 30%, at least about 50%, at least about 70%, 80%, 90%, 95% or higher of the MALTA-like or a MYB-like protein's activity. Methods for measuring activity of MALTA-like or MYB-like polypeptides are well known in the art and have been extensively documented. For example, the DNA binding activity of a MYB-like polypeptide to a consensus target nucleotide sequence, including an inverted CCAAT-box target nucleotide sequence can be determined by in vitro electrophoretic gel mobility shift assay (EMSA) (see, e.g., Lang and Elvira, Nucl. Acids Res. 38(19): 6404-6417, 2010; Li and Parish, Plant J. 8(6):963-72, 1995; Konig et al., Nucl. Acids Res. 26 (7): 1731-1740, 1998; Feldbrügge et al., Plant J. 11(5):1079-93, 1997; and Mohrmann et al., J. Biol. Chem. 277:47385-47392, 2002); or DNA foot-printing analyses (see, e.g., Lang and Elvira, Nucleic Acids Res. 38(19): 6404-6417, 2010; Konig et al., Nucl. Acids Res. 26 (7): 1731-1740, 1998). Other examples of techniques that can be used in measuring biological activity of a MYB-like domain transcription factor include assessing transcriptional activation of a reporter gene that is placed under control of a consensus binding site of the MYB-like transcription factor as described in, for example, Siu et al., Mol. Cell. Biol. 12(4):1592, 1992.

Further, a nucleic acid molecule as provided herein, including a nucleic acid molecule that includes sequences that encode fragments of a MALTA-like or MYB-like domain polypeptide, can be expressed in a recombinant host cell and the effects of expression of the nucleic acid molecule on the organism's productivity can be assayed. Productivity can be measured, for example, by growth assays (e.g., monitoring propagation by cell counts or optical density), by determining total organic carbon (TOC) of ash-free dry weight accumulated over time, or by assessing the amount of any product of interest, for example, proteins, carbohydrates, lipids, pigments, etc. using methods used in the art, including without limitation, gas chromatography (GC), HPLC, immunological detection, biochemical and/or enzymatic detection, etc.

Also of interest in the present invention are variants of the polynucleotides provided herein. Such variants may be naturally-occurring, including homologous polynucleotides from the same or a different species, or may be non-natural variants, for example polynucleotides synthesized using chemical synthesis methods, or generated using recombinant DNA techniques. With respect to nucleotide sequences, degeneracy of the genetic code provides the possibility to substitute at least one base of the protein encoding sequence of a gene with a different base without causing the amino acid sequence of the polypeptide produced from the gene to be changed. Hence, the DNA of the present invention may also have any base sequence that has been changed from any polynucleotide sequence set forth in the Sequence Listing by substitution in accordance with degeneracy of the genetic code. References describing codon usage are readily available.

In addition, the skilled artisan will further appreciate that changes can be introduced by mutation of the nucleotide sequences of the invention, thereby leading to changes in the amino acid sequence of the encoded MALTA-like or MYB-like domain polypeptides, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted nonessential amino acid residues. A "nonessential" amino acid residue, as used herein, is a residue that can be altered from the wild-type sequence of a presently disclosed MALTA-like protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In a particular non-limiting exemplification, conserved residues, domains and motifs of a MALTA-like or MYB-like domain polypeptide disclosed herein. As discussed above, it will be appreciated by one skilled in the art that amino acid substitutions may be made in non-conserved regions that retain the function of the polypeptide. In general, such substitutions would not be made for conserved amino acid residues, or for amino acid residues residing within a conserved motif, where such residues may be essential for protein activity. Examples of residues that are conserved and that may be essential for protein activity include, for example, residues that are identical between all proteins contained in an alignment of the amino acid sequences of the present invention and known MYB-like protein sequences. Examples of residues that are conserved but that may allow conservative amino acid substitutions and still retain activity include, for example, residues that have only conservative substitutions between all proteins contained in an alignment of the amino acid sequences of the present invention and known MYB-like sequences. However, one of skill in the art would understand that functional variants may have minor conserved or non-conserved alterations in the conserved residues.

MALTA variants include proteins having an amino acid sequence that differs from SEQ ID NO:4 by at least one amino acid deletion, insertion, or substitution at one or more of the positions corresponding to the conserved amino acid residues, and combinations of any thereof. In some preferred embodiments, such MALTA variants include proteins having an amino acid sequence that differs from SEQ ID NO:4 by an amino acid deletion, insertion, or substitution at one or more of the positions corresponding to the conserved amino acid residues, and combinations of any thereof. Alternatively or in addition, variant nucleotide sequences can be made by introducing mutations randomly along all or part of the coding sequence, such as by saturation mutagenesis, and the resultant mutants can subsequently be screened for ability to confer activity of an MALTA-like or MYB-like domain protein, in order to identify mutants that retain MALTA-like or MYB-like domain protein activity. For example, following mutagenesis, the encoded protein can be expressed recombinantly, and the activity of the protein can be determined using standard assay techniques as disclosed hereinabove.

Methods for such manipulations are known in the art. For example, amino acid sequence variants of a MALTA-like or MYB-like domain protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired MALTA-like or MYB-like domain activity. However, it is understood that the ability of a MALTA-like or MYB-like domain polypeptide to confer an increase in productivity may be improved by the use of such techniques upon the compositions of this invention. For example, one may express a MALTA-like or MYB-like domain polypeptide in host cells that exhibit high rates of base-misincorporation during DNA replication, such as Stratagene XL-1 Red cell (Fischer Scientific). After propagation in such strains or cells, one can isolate the MALTA-like or MYB-like domain encoding DNA (for example by preparing plasmid DNA, or by amplifying by PCR and cloning the resulting PCR fragment into a vector), followed by culture the mutated MALTA-like or MYB-like domain genes in a non-mutagenic strain or cell, and identify mutated MALTA-like or MYB-like domain genes with an ability to increase host cell productivity, for example by performing an assay to test for MALTA-like or MYB-like domain activity in vivo and in vitro.

Alternatively or in addition, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, (3) target secretion or translation of a protein to a subcellular organelle, such as the periplasmic space of Gram-negative bacteria, or the endoplasmic reticulum of eukaryotic cells, the latter of which often results in glycosylation of the protein.

Domain swapping or shuffling is another mechanism for generating altered MALTA-like or MYB-like domain proteins. Conversed domains may be swapped between MALTA-like or MYB-like domain proteins, resulting in hybrid or chimeric MALTA-like or MYB-like domain polypeptides with improved biomass productivity. Methods for generating recombinant proteins and testing them for improved biomass productivity are known in the art. Accordingly, the molecules of the present invention also include fusions between two or more MALTA-like or MYB-like domain genes or polypeptides. Different domains of different genes or polypeptides can be fused. MALTA-like or MYB-like domain gene fusions can be linked directly or can be attached by additional amino acids that link the two of more fusion partners.

Gene fusions can be generated by basic recombinant DNA techniques, examples of which are described below herein. Selection of gene fusions will depend on the desired phenotype caused by the gene fusion. For instance, if phenotypes associated with the A domain of one MALTA-like or MYB-like protein are desired with phenotypes associated with the B domain of a second MALTA-like or MYB-like protein, a fusion of the first MALTA-like or MYB-like protein's A domain to the second MALTA-like or MYB-like protein's B domain would be created. The fusion can subsequently be tested in vitro or in vivo for the desired phenotypes.

MALTA-like or MYB-like domain polypeptides are also encompassed within the present invention. In an embodiment of this aspect, by "MALTA-like polypeptide" is intended a polypeptide having an amino acid sequence comprising SEQ ID NO:4 and variants thereof. Fragments, biologically active portions, and variants thereof are also provided, and may be used to practice the methods of the present invention.

Altered or improved variants: It is contemplated that DNA sequences of a MALTA-like or other MYB-like transcription factor may be altered by various methods, and that these alterations may result in DNA sequences encoding proteins with amino acid sequences different than that encoded by a MALTA-like gene of the present invention. The MALTA-like or MYB-like domain protein may be altered in various ways including amino acid substitutions, deletions, truncations, and insertions of one or more amino acids of the polypeptide sequences disclosed herein such as, for example, those of SEQ ID NO:4, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Also considered are polypeptides having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4, or to a fragment or conserved domain thereof such as, for example, a DNA-binding domain or SEQ ID NO:2. The polypeptides will preferably be biologically active with respect to either a structural attribute, such as the capacity of a polypeptide to be bound by an antibody or to bind to a target nucleotide sequence (or to compete with another molecule for such binding). Alternatively or in addition, such an attribute may be catalytic and thus involve the capacity of the molecule to mediate a chemical reaction (for an enzymatic protein) or transcriptional regulation response (for a transcription factor). The polypeptides and polypeptides of the present invention may also be recombinant.

In general, the biological activity or biological action of a protein or domain refers to any function(s) exhibited or performed by the protein or domain that is ascribed to the naturally-occurring form of the protein as measured or observed in vivo (i.e., in the natural physiological environment of the protein) or in vitro (i.e., under laboratory conditions). As used herein, a functional domain of a MALTA-like polypeptide is a domain that is capable of performing a biological function of a MALTA-like polypeptide. For example, a biological activity of a MALTA-like polypeptide and the individual domains that make up a MALTA-like polypeptide includes the MYB-like DNA-binding domain, which has been discussed in detail elsewhere herein.

Any of a variety of methods well known in the art may be used to make or to obtain one or more of the above-described polypeptides. The polypeptides of the invention can be chemically synthesized or polypeptides can be made using standard recombinant techniques in heterologous expression systems such as *E. coli*, yeast, insects, etc. Antibodies to the polypeptides of the present invention, or to variants or fragments thereof, are also encompassed. A variety of techniques and methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265), and can be used to make an antibody according to the invention disclosed herein.

Nucleic Acid Constructs

Another aspect of the present invention relates to recombinant nucleic acid molecules comprising a nucleic acid sequence encoding an amino acid sequence having a biological activity of at least one domain of a MALTA-like or MYB-like domain polypeptide as described herein. Typically, such a recombinant nucleic acid molecule includes at least one nucleic acid molecule of the present invention operably linked to one or more heterologous transcription control sequences. A heterologous transcription control sequence can be from the same species as the MALTA-like or MYB-like domain polypeptide (and, for example, associated in the genome with a different gene) or can be from a different species but operable in the species from which the MALTA-like or MYB-like domain polypeptide is derived. As used herein, the phrase "recombinant molecule" or "recombinant nucleic acid molecule" primarily refers to a nucleic acid molecule or nucleic acid sequence operably linked to a transcription control sequence, but can be used interchangeably with the phrase "nucleic acid molecule", when such nucleic acid molecule is a recombinant molecule as discussed herein.

The invention provides nucleic acid constructs comprising a nucleic acid sequence as provided herein operably linked to one or more sequences that can regulate or mediate transcription, translation, or integration of nucleotide sequences into a host genome. For example, the invention provides expression constructs that comprise one or more "expression control elements" or sequences that regulate expression transcription of an operably linked gene, or translation of the transcribed RNA. For example, an expression control element can be a promoter that can be operably linked to a gene of interest or antisense sequence in an expression construct or "expression cassette". Various algal promoters are known and can be used, including those disclosed in U.S. Patent Appl. Pub. No. US 2013/0023035; U.S. patent application Ser. No. 13/486,930, filed Jun. 1, 2012; U.S. patent application Ser. No. 13/693,585, filed Dec. 4, 2012; and U.S. patent application Ser. No. 13/915,522, filed Jun. 11, 2013. A promoter used in a construct may in some instances be regulatable, e.g., inducible.

An inducible promoter can be responsive to, e.g., light intensity or high or low temperature, and/or can be responsive to specific compounds. The inducible promoter may be, for example, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (e.g., U.S. Pat. No. 8,318,482; U.S. Pat. No. 5,750,385; U.S. Pat. No. 5,639,952), metals (*Eukaryotic Cell* 2:995-1002 (2003)) or temperature (U.S. Pat. No. 5,447,858; Abe et al. *Plant Cell Physiol*. 49: 625-632 (2008); Shroda et al. *Plant J*. 21: 121-131 (2000). The foregoing examples are not limiting as to the types of promoters or specific promoters that may be used. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

In aspects where the nucleic acid construct does not contain a promoter in operable linkage with the nucleic acid sequence encoding the gene of interest (e.g., a MALTA-like gene) the nucleic acid sequence can be transformed into the cells such that it becomes operably linked to an endogenous promoter by, e.g., homologous recombination, site specific integration, and/or vector integration. In some instances, genomic host sequences included in a nucleic acid construct for mediating homologous recombination into the host genome may include gene regulatory sequences, for example, a promoter sequence, that can regulate expression of a gene or antisense or RNAi sequence of the nucleic acid construct. In such examples, the transgene(s) of the construct can become operably linked to a promoter that is endogenous to the host microorganism. The endogenous promoter(s) may be regulatable, e.g., inducible.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell. Yet in other embodiments, a recombinant molecule of the present invention comprises an organelle targeting signal to enable an expressed protein to be transported and delivered to the target cellular organelle. It will be appreciated by one skilled in the art that a variety of organelle targeting signals can be used including, but not limited to, nuclear localization signal (NLS), chloroplast targeting signal, and mitochondria-targeting sequence.

A nucleic acid molecule as described herein can be cloned into suitable vector and can be used to transform or transfect any suitable host. The selection of vectors and methods to construct them are commonly known to the art and are described in general technical references (see, e.g., Sambrook and Russell, *Molecular Cloning, A Laboratory Manual*, Cold Spring Harbor Laboratory Press, 2001). Thus, in some embodiments of the invention, the recombinant nucleic acid molecule is a recombinant vector. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences. The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native, or plasmid promoter control, or under a combination of several promoter controls. Single or multiple copies of the nucleic acid molecule can be integrated into the chromosome. A recombinant vector of the present invention can contain one or more selectable genetic markers.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption, modification, or knock-out technology). Such a vector may also be known in the art as a "knock-out" vector. In one aspect of this embodiment, a portion of the vector, which is typically the nucleic acid molecule inserted into the vector (i.e., the insert), has a nucleic acid sequence that is homologous to a nucleic acid sequence of a target gene in the host cell (i.e., a gene which is targeted to be modified, deleted, or inactivated). The nucleic acid sequence of the vector insert is designed to bind to the target gene such that the target gene and the insert undergo homologous recombination, whereby the endogenous target gene is modified, deleted, inactivated or attenuated (i.e., by at least a portion of the endogenous target gene being mutated or deleted).

Constructs for homologous recombination into an algal or heterokont genome (e.g., for disruption or gene replacement of a regulator gene) can include a nucleotide sequence of a MALTA-like gene or ortholog, such as for example any provided herein, or sequences from the algal or heterokont genome that are adjacent to the MALTA-like gene in the host organism. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a gene targeted for knock-out or gene replacement such as a MALTA-like gene or ortholog, such as any disclosed herein, and/or genomic DNA adjacent thereto. For example, the sequences for mediating homologous recombination in a construct can include one or more nucleotide sequences from or adjacent to a naturally-occurring algal or heterokont gene encoding a MALTA-like polypeptide, wherein the MALTA-like polypeptide comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to SEQ ID NO:2 or SEQ ID NO:4. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:3; and/or an adjacent region of the corresponding genome.

For example, the sequences for mediating homologous recombination in a construct can include one or more nucleotide sequences from or adjacent to a naturally-occurring algal or heterokont gene encoding a MALTA-like polypeptide, wherein the MALTA-like polypeptide comprises an amino acid sequence having at least 80%, for example, at least 85%, at least 90%, at least 95% identity, or at least 99% to the amino acid set forth in SEQ ID NO:4. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a regulator gene that encodes a MALTA-like polypeptide, such as any disclosed herein, and/or genomic DNA adjacent thereto. For example, the sequences for mediating homologous recombination in a construct can include one or more nucleotide sequences from or adjacent to a naturally-occurring algal or heterokont gene encoding a MYB-like DNA-binding domain-containing protein, wherein the MYB-like DNA-binding domain-containing protein comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to any one of the MYB-like DNA-binding domain SEQ ID NO:2. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of any one of the nucleic acid sequences encoding a MYB-like DNA-binding domain disclosed herein and/or an adjacent region of the corresponding genome.

General discussion above with regard to recombinant nucleic acid molecules and transformation of host cells is intended to be applied to any recombinant nucleic acid molecule discussed herein, including those encoding any amino acid sequence having a biological activity of at least one domain from a MALTA-like polypeptide, those encoding amino acid sequences from other MALTA-like polypeptides, and those encoding other proteins or domains.

Use of the Nucleic Acid Molecules of the Invention

In one aspect of the invention, one may use one of many known methods to identify DNA sequences adjacent to polynucleotide sequences of interest, such as genomic regions that naturally surround a novel polynucleotide sequence in microbial cell or plant cell. One may accomplish this by generating hybridization probes and screening an existing library of chromosomal DNA for clones likely to contain DNA adjacent to the novel polynucleotide sequence of interest. Alternatively or in addition, one may clone and sequence regions flanking a known DNA by inverse PCR (Sambrook et al., 1989, supra). Another such method involves ligating linkers of known sequence to chromosomal DNA digested with restriction enzymes, then generating PCR product using an oligonucleotide homologous to the primer linker, and a primer homologous to the region of interest (e.g. the end sequence of a novel polynucleotide sequence of the invention). A kit for performing this procedure (GENOMEWALKER™, Clonetech) is available commercially.

In a hybridization procedure, all or part of a presently disclosed MALTA-like or MYB-like protein encoding nucleotide sequence can be used to screen cDNA or genomic libraries. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known MYB-like protein encoding nucleotide sequence disclosed herein. Degenerate primers designed on the basis of conserved nucleotides or amino acid residues in the nucleotide sequence or encoded amino acid sequence can optionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of a MALTA-like or MYB-like protein-encoding nucleotide sequence of the invention or a fragment or variant thereof. Methods for the preparation of probes for hybridization are generally known in the art and are disclosed in Sambrook and Russell (2001, supra) herein incorporated by reference.

Recombinant Microorganism

The invention also provides a recombinant microorganism that includes a non-native gene that encodes a MALTA-like protein as disclosed herein. The recombinant microorganism can have a higher productivity than does a control microorganism substantially identical to the recombinant microorganism except that the control microorganism does not have a non-native gene encoding a MALTA-like or MYB-like protein. A MALTA-like protein can be any MALTA-like protein, such as, for example, a MALTA-like protein whose sequence is available from gene, protein, or genome databases or scientific literature, or a variant thereof. In some example, a recombinant microorganism as provided herein can in some examples include a MALTA-like or MYB-like protein as provided herein, for example, can include any of SEQ ID NO:2; SEQ ID NO:4 or a functional fragment or variant thereof having productivity-enhancing activity when produced in a host cell.

In various examples, a recombinant microorganism as provided herein includes a non-native gene that encodes a polypeptide having an amino acid sequence with at least 65%, at least 70%, at least 75%, at least 80%, at least 85%, at least 90%, at least 95%, at least 96%, at least 97%, at least 98%, or at least 99% identity to a MYB-like domain of SEQ ID NO:2. The polypeptide encoded by the non-native gene is preferably a MALTA-like protein, such as a polypeptide having at least 50% identity to a naturally-occurring MALTA-like protein of a plant or microorganism. The polypeptide can have, for example, at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4. In some examples, the non-native gene encodes a polypeptide having a MYB-like DNA-binding domain in which the polypeptide has at least 50%, at least 55%, at least 60%, at least 65%, at least 70%, at least 75%, at least 80%, at least 85%, at least 90%, at least 95%, at least 96%, at least 97%, at least 98%, or at least 99% identity to a MALTA-like polypeptide of a microalgal or heterokont species. The recombinant microorganism can exhibit higher productivity than is exhibited by a control microorganism substantially identical to the recombinant microorganism that includes the non-native gene encoding a polypeptide having a MYB-like DNA-binding domain, with the exception that the control microorganism does not include a non-native gene encoding a polypeptide having a MYB-like DNA-binding domain. For example, expression of the non-native gene in an algal or heterokont cell can result in the algal or heterokont cell producing a greater amount of biomass or a greater amount of one or more biomolecules, such as, without limitation, a lipid, a terpenoid, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a pigment or colorant.

A recombinant microorganism having a non-native gene encoding a polypeptide having a MYB-like DNA-binding domain can comprise, e.g., any of the nucleic acid molecules described herein that encode a polypeptide that includes a MYB-like DNA-binding domain. Further, the recombinant host cells may comprise any of the constructs or vectors described herein. In some aspects, the nucleic acid sequence encoding the polypeptide can be heterologous with respect to the recombinant host cell, and can be a gene encoding a MALTA-like polypeptide derived from any species, including a plant, animal, or microbial species, or a variant thereof. Alternatively, the gene encoding a MALTA-like polypeptide may be homologous with respect to the host organism. For example, the non-native MALTA-like gene may be a MALTA-like gene of the same species as the host microorganism and is introduced into the recombinant microorganism in an expression cassette that allows regulated expression or overexpression of the introduced homologous MALTA-like gene. Alternatively, the MALTA-like non-native gene may be endogenous to the microorganism and a heterologous promoter may be introduced into the host microorganism such that it becomes juxtaposed with and operably linked to the endogenous MALTA-like gene to effect overexpression and/or regulated expression.

In further examples, a recombinant microorganism as provided herein can include a non-native gene that encodes a polypeptide having a MYB-like DNA-binding domain, such as a MYB-like DNA-binding domain having at least 85%, at least 90%, at least 95%, at least 96%, at least 97%, at least 98%, or at least 99% identity to the amino acid sequence of SEQ ID NO:2. The polypeptide encoded by the non-native gene can have, for example, at least 65%, at least 70%, at least 75%, at least 80%, at least 85%, at least 90%, at least 95%, at least 96%, at least 97%, at least 98%, or at least 99% identity to the amino acid sequence of SEQ ID NO:4.

In particular examples, a recombinant microorganism as provided herein can include a non-native gene that encodes a polypeptide having at least 85%, at least 90%, at least 95%, at least 96%, at least 97%, at least 98%, or at least 99% identity to the amino acid sequence of SEQ ID NO:4, where the polypeptide includes a MYB-like DNA-binding domain having at least 85%, at least 90%, at least 95%, at least 96%, at least 97%, at least 98%, or at least 99% identity to the amino acid sequence of SEQ ID NO:2.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes from either the nucleus or the plastid, and in some cases can result in transient expression of transgenes. For example, genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell*, 2010; and Gong et al., *J. Ind. Microbiol. Biotechnol.*, 2011). Non-limiting examples of such useful transformation methods include agitation of cells in the presence of glass beads or silicon carbide whiskers as reported by, for example, Dunahay, *Biotechniques*, 15(3):452-460, 1993; Kindle, *Proc. Natl. Acad. Sci. U.S.A.*, 1990; Michael and Miller, *Plant J.*, 13, 427-435, 1998. Electroporation techniques have been successfully used for genetic transformation of several microalgal species including *Nannochloropsis* sp. (see, e.g., Chen et al., *J. Phycol.*, 44:768-76, 2008), *Chlorella* sp. (see, e.g., Chen et al., *Curr. Genet.*, 39:365-370, 2001; Chow and Tung, *Plant Cell Rep.* Vol. 18, No. 9, 778-780, 1999), *Chlamydomonas* (Shimogawara et al., *Genetics*, 148: 1821-1828, 1998), *Dunaliella* (Sun et al., *Mol. Biotechnol.*, 30(3): 185-192, 2005). Micro-projectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.*, 252:572-579, 1996), *Cyclotella* and *Navicula* (Dunahay et al., *J. Phycol.*, 31:1004-1012, 1995), *Cylindrotheca* (Fischer et al., *J. Phycol.*, 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., *Protist*, 155:381-93, 2004). Additionally, *Agrobacterium*-mediated gene transfer techniques can also be useful for genetic transformation of microalgae, as has been reported by, for example, Kumar, *Plant Sci.*, 166(3):731-738, 2004, and Cheney et al., *J. Phycol.*, Vol. 37, Suppl. 11, 2001.

A transformation vector as described herein will typically comprise a marker gene that confers a selectable or scorable phenotype on target host cells, e.g., algal cells. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.*, 19, 353-61, 1999, Lumbreras et al., *Plant J.*, 14(4):441-447, 1998; Zaslayskaia et al., *J. Phycol.*, 36:379-386, 2000), spectinomycin (Cerutti et al., *Genetics*, 145: 97-110, 1997; Doetsch et al., *Curr. Genet.*, 39, 49-60, 2001; Fargo, *Mol. Cell. Biol.*, 19:6980-90, 1999), streptomycin (Berthold et al., *Protist*, 153:401-412, 2002), paromomycin (Jakobiak et al., *Protist*, supra.; Sizova et al., *Gene*, 277:221-229, 2001), nourseothricin (Zaslayskaia et al., 2000, supra), G418 (Dunahay et al., 1995, supra; Poulsen and Kroger, *FEBS Lett.*, 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paramomycin and neomycin resistance (Sizova et al., 2001, supra). Other fluorescent or chromogenic markers that have been used include luciferase (Falciatore et al., *J. Mar. Biotechnol.*, 1: 239-251, 1999; Fuhrmann et al., *Plant Mol. Biol.*, 2004; Jarvis and Brown, *Curr. Genet.*, 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.*, 1:165-169, 1994), β-galactosidase (Gan et al., *J. Appl. Phycol.*, 15:345-349, 2003; Jiang et al., *Plant Cell Rep.*, 21:1211-1216, 2003; Qin et al., *High Technol. Lett.*, 13:87-89, 2003), and green fluorescent protein (GFP) (Cheney et al., 2001, supra; Ender et al., *Plant Cell*, 2002, Franklin et al., *Plant J.*, 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.*, 18:778-780, 1999; Jarvis and Brown, *Curr. Genet.*, 317-321, 1991; Lohuis and Miller, *Plant J.*, 13:427-435, 1998). The SV40 promoter from simian virus has also reported to be active in several algae (Gan et al., *J. Appl. Phycol.*, 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.*, 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.*, 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.*, 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272: 3413-3423, 2005), thus gene expression can be switched off or on when microalgal cells are grown in the presence of ammonium/nitrate. Additional algal promoters that can find use in the constructs and transformation systems provided herein include those disclosed in U.S. Patent Appl. Pub. No. US 2013/0023035; U.S. patent application Ser. No. 13/486,930, filed Jun. 1, 2012; U.S. patent application Ser. No. 13/693,585, filed Dec. 4, 2012; and U.S. patent application Ser. No. 13/915,522, filed Jun. 11, 2013.

Host cells can be either untransformed cells or cells that are already transfected with at least one nucleic acid molecule. For example, a host cell that includes a non-native gene as provided herein that encodes a MALTA-like gene, homolog, or variant can further include one or more genes that may confer any desirable trait, such as, but not limited to, increased production of biomolecules of interest, such as one or more proteins, pigments, alcohols, or lipids. For example, for production of lipid, a host cell (such as but not limited to an algal or heterokont host cell) can optionally include one or more non-native genes encoding polypeptides that functions in lipid biosynthesis, including, but not limited to, polypeptides that encode enzymes for the production of fatty acids, fatty acid derivatives, and/or glycerolipids including, but not limited to, diacylglycerol acyltransferase (DGAT) gene, a glycerolphosphate acyltransferase (GPAT) gene, a lysophosphatidic acid acyltransferase (dehydrogenase) (LPAAT) gene, a phosphatidic acid phosphatase (PAP) gene, and/or a monoacylglycerol acyltransferase (MGAT) gene.

Suitable host cells to be modified using the materials and methods according to the present invention include, but are not limited to, bacteria, protists, microalgae, phytoplankton, heterokonts, fungi, and protozoa. The process can be used, for example, with algal species that are important or interesting for aquaculture, or for the production of biomass used in producing liquid fuel molecules and other chemicals.

Heterokont species considered for use in the invention include, but are not limited to, *Bacillariophytes, Eustigmatophytes, Labrinthulids*, and *Thraustochytrids*. In some examples, the strain may be a species of *Labryinthula, Labryinthuloides, Thraustochytrium, Schizochytrium, Aplanochytrium, Aurantiochytrium, Japonochytrium, Diplophrys*, or *Ulkenia*.

Algal species suitable for the method of the invention include microalgae such as, for example, a species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Cryptohecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phœodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

In some embodiments of the present application, preferred microorganisms to genetically engineer include, but are not limited to, photosynthetic organisms such as cyanobacteria, algae, diatoms, and the like. Non-limiting examples of exemplary species include, for instance, eustigmatophytes or diatoms such as, for example, a species of *Amphora, Chaetoceros, Cyclotella, Eustigmatos, Fragilaria, Fragilaropsis, Monodus, Nannochloropsis, Navicula, Nitzschia, Pavlova, Phœodactylum, Thalassiosira*, or *Vischeria*. In some embodiments, members of the genus *Nannochloropsis* such as, but are not limited to, *N. gaditana, N. granulata, N. limnetica, N. oceanica, N. oculata*, and *N. salina* are transformed with or overexpress a nucleic acid molecule as provided herein that encodes a MALTA-like or MYB-like domain polypeptide.

A microorganism that includes a non-native gene as provided herein can have improved productivity when compared with a control microorganism that does not include the non-native gene encoding a MYB-like DNA-binding domain-containing polypeptide. Higher productivity can be demonstrated by measuring growth rates, for example, using a cytometer, or by measuring optical density at wavelengths higher than 700 nm, for example, at 730 or 750 nm. Ash free dry weight can also be measured, as provided in the Examples herein. Production of various biomolecules can be assessed by extraction of algal biomass, partial or substantial purification of the product of the biomolecule of interest, and quantitation of the product by any means known in the art, such as but not limited to, chemical or biochemical analysis, spectroscopic or immunological detection, and/or activity assays.

Methods of Producing Algal Products

Also provided herein are methods of producing biomass or at least one bioproduct by culturing microbial cells having a modulated growth characteristic, such as the host cells disclosed herein. The methods include culturing a microbial cell as disclosed herein that includes a non-native gene encoding a MALTA-like protein, such as a nucleic acid molecule as disclosed herein that encodes a MALTA-like or MYB-like domain protein, in a suitable medium to provide an algal culture and recovering biomass or at least one bioproduct from the culture. The microorganism in some examples can be a microalga. The algal culture can be a photoautotrophic culture, in which the culture medium preferably does not include a substantial amount of reduced carbon, that is, the culture does not include reduced carbon in a form or at a level that can be used by the algae for growth.

The algae may be cultured in any suitable vessel, including flasks or bioreactors, where the algae may be exposed to artificial or natural light. The culture comprising algal cells with modulated growth characteristics may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the host cells provided herein having modulated growth characteristics can achieve higher cell density of the culture over time, for example, over a period of a week or more, with respect to a culture wild-type algal cells of the same strain that are not modulated in growth characteristics. For example, a host cell of the invention as described herein may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) *Algae: Anatomy, Biochemistry & Biotechnology*, CRC Press, for media and methods for culturing algae. Algal media recipes can also be found at the websites of various algal culture collections, including, as non-limiting examples, the UTEX Culture Collection of Algae (sbs.utexas.edu/utex/media.aspx); Culture Collection of Algae and Protozoa (ccap.ac.uk); and Katedra Botaniky (botany.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms having a modulated growth characteristic as described herein can be cultured in a fermenter or bioreactor, where the bioreactor can optionally be a "photobioreactor" equipped with an artificial light source, and/or having one or more walls that is transparent enough to light, including sunlight, to enable, facilitate, and/or maintain photosynthetic microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, recombinant photosynthetic microorganisms or host cells may be grown in ponds, canals, sea-based growth containers, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

Biomass of the microorganism culture can be recovered by harvesting the microorganism from the medium, for example, by filtering, settling, centrifugation, or combinations thereof. In biomass production embodiments according to the invention, the amount of the biomass produced and/or recovered by the method described herein, measured as ash free dry weight (AFDW) can advantageously be at least about 0.05 g per liter of culture, for example at least about 0.1 g, at least about 0.2 g, at least about 0.3 g, at least about 0.4 g, at least about 0.5 g, at least about 0.6 g, at least about 0.7 g per liter of culture, at least about 1 g per liter of culture, at least about 1.5 g per liter of culture, at least about 2 g per liter of culture, at least about 2.5 g per liter of culture, or at least about 5 g per liter of culture. Although many times the goal can be to produce and/or recover as much biomass as possible, in some instances the amount of the biomass produced and/or recovered by the method described herein, measured as ash free dry weigh (AFDW) can be limited to about 15 g or less per liter of culture, for example about 12 g or less per liter of culture, about 10 g or less per liter of culture, about 5 g or less per liter of culture, about 2 g or less per liter of culture, about 1 g or less per liter of culture, or about 0.5 g or less per liter of culture.

Biomass can be harvested, for example, by centrifugation or filtering. The biomass may be dried and/or frozen. Further products may be isolated from biomass, such as, for example, lipids or one or more proteins. Thus, also provided in an aspect of the invention is an algal biomass comprising an algal host cell having modulated growth and/or phenotypic characteristics, such as any of the recombinant host cells disclosed herein, for example, an algal host cell comprising a nucleic acid molecule of the invention wherein elevated expression of the nucleic acid molecule results in higher biomass productivity.

Biomass can be used in any of a number of ways, for example, it can be processed for use as a biofuel by generating syngas from the biomass, can be supplied to an anaerobic digester for production of one or more alcohols, or the biomass can be extracted to provide algal lipids, such as but not limited to monoglycerides, diglycerides, or triglycerides, fatty acid alkyl esters, fatty acids, and/or fatty acid derivatives.

The host algal cell as described herein can include one or more non-native genes encoding a polypeptide for the production of a product, such as, but limited to, a lipid, a colorant or pigment, an antioxidant, a vitamin, a nucleotide, an nucleic acid, an amino acid, a hormone, a cytokine, a peptide, a protein, or a polymer. For example, a non-native gene can encode an enzyme, metabolic regulator, cofactor, carrier protein, or transporter.

In some embodiments, products such as fatty acids and fatty acid derivatives can be recovered from culture by recovery means known to those of ordinary skill in the art, such as by whole culture extraction, for example, using organic solvents. In some cases, recovery of fatty acids or fatty acid derivatives (such as fatty acid esters) can be enhanced by homogenization of the cells, as provided in the examples herein. When fatty acids are sufficiently released from the microorganisms into the culture medium, the recovery method can be adapted to efficiently recover only the released fatty acids, only the fatty acids produced and stored within the microorganisms, or both the produced and released fatty acids.

In further embodiments, products such as but not limited to free fatty acids and fatty acid derivatives that are secreted/released into the culture medium by the recombinant microorganisms described above can be recovered in a variety of ways. A straightforward isolation method, e.g., by partition using immiscible solvents, may be employed. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acids can then be eluted from the particulate adsorbents, e.g., by the use of an appropriate solvent. In such circumstances, one isolation method can include carrying out evaporation of the solvent, followed by further processing of the isolated fatty acids and lipids, to yield chemicals and/or fuels that can be used for a variety of commercial purposes.

Some embodiments of the invention concern methods that comprise culturing an algal host cell as described herein that further includes at least one non-native gene encoding a polypeptide that participates in the production of a product, to produce biomass or at least one algal product. Products such as lipids and proteins can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending U.S. Patent Application Publication 2013/entitled "Solvent Extraction of Products from Algae", filed on Feb. 29, 2012, which is incorporated herein by reference in its entirety.

Alternatively or in addition to any of the embodiments described herein, the following embodiments are provided.

Embodiment 1 includes an isolated or recombinant nucleic acid molecule that encodes a polypeptide that:
recruits to pfam PF00249; or
includes an amino acid sequence having at least 65%, at least 70%, at least 75%, at least 80%, at least 85%, at least 90%, at least 95%, at least 96%, at least 97%, at least 98%, or at least 99% identity to SEQ ID NO:2;
wherein, the isolated or recombinant nucleic acid molecule can optionally comprise a nucleotide sequence having at least 50%, at least 55%, at least 65%, at least 70%, at least 75%, at least 80%, at least 85%, at least 90%, at least 95%, at least 96%, at least 97%, at least 98%, or at least 99% identity to SEQ ID NO:3 or SEQ ID NO:16, and
further optionally wherein the encoded polypeptide has at least 75%, at least 80%, at least 85%, at least 90%, at least 95%, at least 96%, at least 97%, at least 98%, or at least 99% identity to SEQ ID NO:4.

Embodiment 2 includes an isolated or recombinant nucleic acid molecule according to Embodiment 1, wherein elevated expression of the isolated or recombinant nucleic acid molecule in a genetically modified microorganism results in any of increased biomass productivity, increased growth rate, or increased bioproduct made by the genetically modified microorganism, wherein the bioproduct can optionally be any of a nucleotide, an amino acid, a polypeptide, a cofactor, a hormone, a pigment or colorant, an antioxidant, a vitamin, an oil, a lipid, a fatty acid, a fatty alcohol, a fatty aldehyde, a fatty acid ester, a wax ester, a hydrocarbon, a triacylglyceride, a diacylglyceride, a monoacylglyceride, a phospholipid, or a terpenoid.

Embodiment 3 includes an isolated or recombinant nucleic acid molecule according to Embodiment 1 or Embodiment 2 operably linked to a heterologous sequence that regulates expression of the nucleic acid molecule.

Embodiment 4 includes an isolated or recombinant nucleic acid molecule according to any of Embodiments 1-3, wherein the isolated or recombinant nucleic acid molecule comprises a vector that includes one or more of a reporter gene, selectable marker, origin of replication, and sequence for mediating homologous recombination into the genome of an organism.

Embodiment 5 includes a host cell that includes a non-native nucleic acid molecule according to any of Embodiments 1-4, where the host cell is a eukaryotic host cell selected from the group consisting of algae cells, heterokont cells, fungal cells, plant cells, animal cells, or insect cells.

Embodiment 6 includes a host cell that includes a non-native nucleic acid molecule according to any of Embodiments 1-4, where the host cell is a eukaryotic host cell selected from the group consisting of algae cells, heterokont cells, fungal cells, plant cells, animal cells, or insect cells.

Embodiment 7 includes a genetically engineered microorganism that includes a non-native gene encoding a polypeptide wherein the polypeptide:

a) comprises an amino acid sequence having at least 65%, at least 70%, at least 75%, at least 80%, at least 85%, at least 90%, at least 95%, at least 96%, at least 97%, at least 98%, or at least 99% identity to SEQ ID NO:2; and/or b) has at least 65%, at least 70%, at least 75%, at least 80%, at least 85%, at least 90%, at least 95%, at least 96%, at least 97%, at least 98%, or at least 99% identity to SEQ ID NO:4;

wherein the genetically engineered microorganism has a higher growth rate or has greater productivity as compared with a control microorganism that does not include the non-native gene according to a) and/or b).

Embodiment 8 includes a genetically engineered microorganism according to Embodiment 7 wherein the non-ntive gene encodes a polypeptide that recruits to pfam PF00249.

Embodiment 9 includes a genetically engineered microorganism according to Embodiment 7 or Embodiment 8 wherein the non-native gene comprises a nucleotide sequence having at least to SEQ ID NO:3 or SEQ ID NO:16.

Embodiment 10 includes a genetically engineered microorganism according to any of Embodiments 7-9 where the microorganism is an alga, optionally belonging to a genus selected from the group consisting of or where the microorganism is a heterokont, optionally belonging to a genus selected from the group consisting of Embodiment 11 includes a method for producing biomass or a bioproduct by culturing a genetically engineered host cell or microorganism according to any of Embodiments 5-10, wherein the bioproduct can optionally be any of a food, feed, biofuel, bio-chemical, pharmaceutical, or medicinal product, further wherein the bioproduct can optionally be an oil, an amino acid, a polypeptide, a cofactor, a hormone, a pigment or colorant, an antioxidant, a vitamin, a lipid, a fatty acid, a fatty alcohol, a fatty aldehyde, a fatty acid ester, a wax ester, a hydrocarbon, a triacylglyceride, a diacylglyceride, a monoacylglyceride, a phospholipid, or a terpenoid; wherein the method optionally includes isolating biomass or a bioproduct from the culture.

Example 12 includes a method for producing biomass or a bioproduct according to claim 11, where the genetically engineered host cell or microorganism is an alga and the alga is cultured mixotrophically or phototrophically.

The discussion of the general methods given herein is intended for illustrative purposes only. Other alternative methods and embodiments will be apparent to those of skill in the art upon review of this disclosure, and are to be included within the spirit and purview of this application.

EXAMPLES

A novel member of the MYB-like transcription factor family has been identified and isolated from the algal strain *Nannochloropsis gaditana* that when overexpressed confers increased productivity in microorganisms. As detailed herein, these discoveries were made by identifying genes encoding transcription factors in the genome of the algal strain *Nannochloropsis* WT-3730, constructing expression vectors including putative transcription factor genes, transforming the expression vectors into *Nannochloropsis*, and analyzing the resulting algal lines for increased productivity.

Example 1

Development of *Nannochloropsis* Recombinant Cells Lines Overexpressing One or More Transcription Factors The algal strain WT-3730 was derived from the strain *Nannochloropsis gaditana* CCMP1894 obtained from the Provasoli-Guillard National Center for Marine Algae and Microbiota (NCMA, Maine, U.S.A.), which is formerly the National Center for Culture of Marine Phytoplankton (CCMP). Whole genomic DNA content of the WT-3730 strain was first isolated and shot-gun sequenced using 454-pyrosequencing methodologies (454 Life Sciences). *Nannochloropsis gaditana* genomic DNA was used for library construction according to the recommended protocol (454 Life Sciences) for single long reads. The sequences were generated by GS FLX Titanium series sequencing runs. Mate-pair and paired-end genomic DNA library construction was performed for Illumina short-read (100 bp) sequencing.

For cDNA sequencing, total RNA was isolated from *Nannochloropsis gaditana* cells using Qiagen RNeasy Maxi™ columns according to the manufacturer's recommendations. cDNA was synthesized by fragmenting the RNA and converting it to cDNA with random primers using the Illumina mRNA-Seq Library Preparation Kit according to the manufacturer's recommendation. Illumina adapters were then ligated to the DNA ends and the sample was PCR amplified using reagents in the same kit. The DNA template was sequenced on an Illumina Genome Analyzer II™ platform according to the manufacturer's recommended conditions. Paired-end reads were generated and mapped to the assembled genome sequence as described below.

Genome sequence assemblies were carried out using Newbler assembler version 2.0.00.20 for the 454-sequence data and using ALLPATHS-LG for the Illumina mate-pair and paired-end data. Coding gene sequences were predicted from assembled genomic contigs using an approach that combined evidence from multiple sources using either the Evigan consensus gene prediction method (Liu et al., *Bioinformatics*, 24(5):597-605, 2008) or Augustus (Stanke et al., *BMC Bioinformatics* 7, 2006). Putative transcription factors were then identified using probabilistic Hidden Markov Models (HMMER version 3; which can be found at hmmer.janelia.org/) with Pfam models on the predicted gene sequences.

In addition to the HMM-based ab initio gene model, further direct evidence on gene structure was included in the predictions using the hints mechanism included in the Augustus program. This mechanism allows providing additional evidence on gene features such as exon-intron boundaries that Augustus can use to determine for example the location of an exon-intron boundary that is both consistent with the ab initio model and is supported by direct experimental data. The evidence used in gene finding process included GeneWise protein-DNA alignments, Solexa based exon-intron splice junctions generated using Tophat, and assembled transcripts created using the program Cufflinks. The weights for all hints were derived by optimizing them using an accuracy function based on the sensitivity and specificity of gene prediction results on *Arabidopsis* genome sequence using the manually curated *Arabidopsis* genome annotation (TAIR database, arabidopsis.org/) as a reference data set. Alternative transcripts for genes were also predicted when the evidence supported their presence.

The whole genome-sequencing data was then assembled and annotated. Genes encoding putative transcription factors were identified bioinformatically by relying mainly on Pfam analyses and Hidden Markov Models (HMM) using the program hmmer3 (janelia.org). The 'Plant Transcription Factor Database' (Perez-Rodriguez et al. (2010) *Nucl. Acids Res*. 38 (Suppl 1): D822-D827) was also used as a reference. The identification of genes encoding transcription factors was performed based upon coding regions (e.g. exons), as the naturally-occurring genes generally included one or more introns that were identified and excluded from the resulting gene sequences. Genes encoding transcription factors identified as such were subsequently constructed as cDNAs from exon sequences and used in the transformation constructs, e.g., SEQ ID NO:3. The amino acid sequence set forth in SEQ ID NO:4 represents the encoded polypeptide of this cDNA.

With the goal in mind of enhancing lipid and or biomass productivity, 74 putative transcription factor genes (cDNAs) were selected and overexpressed in *Nannochloropsis* WT-3730 cells. For this purpose, numerous transformation vectors were constructed in which transcriptional expression of the genes encoding the transcription factors was placed under control of either a TCTP promoter from *Nannochloropsis gaditana* (SEQ ID NO:5), an elongation factor promoter from *Nannochloropsis gaditana* (eIF3, SEQ ID NO:6), or a 60S ribosomal protein L24 promoter from *Nannochloropsis gaditana* (SEQ ID NO:7).

For transformation, *Nannochloropsis gaditana* cells were grown in PM064 media and harvested at a concentration between $1$-$3 \times 10^7$ cells/mL. Cells were centrifuged at 2500×g for 10 minutes at 25° C. to pellet the cells. Cells were then resuspended in a sterile solution of 385 mM sorbitol and centrifuged again, then washed two more times in sorbitol to remove all traces of media. The cell pellet was resuspended in sorbitol to a final concentration of $1 \times 10^{10}$ cells/mL. Linearized plasmid DNA of construct was aliquoted into microfuge tubes at a concentration between 0.5-5 μg DNA, and 100 μL of cell mixture was mixed with the DNA. The mixture was transferred to chilled electroporation cuvettes with a gap distance of 2 mm. The electroporator was set to 50 μF capacitance, 500 ohms resistance and 2.2 kV voltage. Following electroporation, samples were resuspended in 1 mL of sorbitol and incubated on ice for a few minutes. Cells were transferred to 15 mL conical tubes containing 10 mL of fresh media, and allowed to recover overnight in dim light (~5 μmol photons $m^{-2}$ $sec^{-1}$). The next day, cells were plated at a concentration between $5$-$7 \times 10^8$ cells/mL on PM024 plates containing either 5 μg/mL zeocin, 100 μg/mL hygromycin, or 100 μg/mL blasticidin. Plates were incubated under constant light (~80 μmol photons $m^{-2}$ $sec^{-1}$) until colonies appeared (about 2-3 weeks).

PM024 media includes: 35 ppt Instant Ocean Salts (Aquatic Eco Systems; Apopka, Fla.), 10× Guillard's F/2 marine water enrichment solution (50× stock from Sigma-Aldrich, St. Louis, Mo., cat. No. G0154; final concentrations of components in media: 8.825 mM Sodium nitrate; 0.32 mM Sodium phosphate monobasic; 0.205 μM Biotin; 0.420 μM Cobalt chloride.6H$_2$O; 0.400 μM Cupric sulfate.5H$_2$O; 0.11713 mM Disodium EDTA.2H$_2$O; 9.095 μM Manganese chloride.4H$_2$O; 0.248 μM Sodium molybdate.2H$_2$O; 2.965 μM Thiamine.HCl; 0.037 μM Vitamin B$_{12}$; 0.765 μM Zinc sulfate.7H$_2$O).

PM064 media includes: 35 ppt Instant Ocean Salts, 5× Guillard's F/2 marine water enrichment solution (50× stock from Sigma-Aldrich, St. Louis, Mo., cat. No. G0154; final concentrations of components in media: 4.413 mM Sodium nitrate; 0.16 mM Sodium phosphate monobasic; 0.103 μM Biotin; 0.240 μM Cobalt chloride.6H$_2$O; 0.200 μM Cupric sulfate. 5H$_2$O; 0.0585 mM Disodium EDTA.2H$_2$O; 4.54 μM Manganese chloride.4H$_2$O; 0.124 μM Sodium molybdate.2H$_2$O; 1.48 μM Thiamine.HCl; 0.0185 μM Vitamin B$_{12}$; 0.382 μM Zinc sulfate.7H$_2$O).

Example 2

Identification and Isolation of MALTA, a *Nannochloropsis* MYB-Like Transcription Factor Conferring Increased Cell Biomass Productivity Recombinant algal cell lines overexpressing one or more of the transcription factors described in Example 1 were subsequently screened for modulation in cell biomass productivity. Duplicate 25 cm$^2$ flasks containing approximately 30 ml PM066 medium were inoculated with algal cells from 20 ml liquid cultures that had been inoculated from 5 ml cultures started from cells growing on plates. After 3-6 days of growth, the cultures were diluted based on the growth characteristics of the strain such that they were estimated to reach late log phase in 3 days. The flasks were placed in an Adaptis growth chamber, shaking at approximately 130 rpm in an environment containing 1% $CO_2$-enriched air and exposed to approximately 274 μE·m$^{-2}$·s$^{-1}$ light on a 16 h light (at 30° C.):8 h dark (at 25° C.) cycle. After 3 days, these seed cultures were used to inoculate 75 cm$^2$ flasks each containing a 200 ml total culture volume to a density providing approximately 35% light attenuation through the culture (which was 8.6 cm from the side closest to the light to the side farthest from the light). The tops of the flasks were fitted with a cap that included an air bubbling tube and a port used for culture sampling. Cultures were bubbled with 1% $CO_2$-enriched air on a shelf positioned against a light bank providing approximately 550 μE photosynthetically active radiation (PAR) at the front of the centrally positioned flask. The light regime was 16 hours of light (at 30° C.) to 8 hours of darkness (at 25° C.). After two days of growth, 6 mL samples were removed daily for FAME and TOC (total organic carbon) analysis and evaporative losses were made up with sterile distilled water during the seven day culturing period.

PM066 medium included 10 mM nitrate (NO$_3$) and 0.417 mM phosphate (PO$_4$) along with trace metals and vitamins in Instant Ocean salts. PM066 media was made by adding 5.71 ml of a 1.75 M NaNO$_3$ stock solution (148.7 g/L), and 5.41 ml of a 77 mM K$_2$HPO$_4$.3H$_2$O stock solution (17.57 g/L) to 981 mls of Instant Ocean salts solution (35 g/L) along with 4 ml of Chelated Metals Stock Solution and ml of 4 ml Vitamin Stock Solution. Chelated Metals Stock, Solution was prepared by adding to 400 mls of water 2.18 g Na$_2$EDTA.2H$_2$O; 1.575 g FeCl3.6H$_2$O; 500 μl of 39.2 mM stock solution (0.98 g/100 ml) CuSO$_4$.5H$_2$O; 500 μl of 77.5 mM stock solution (2.23 g/100 ml) ZnSO$_4$.7H$_2$O; 500 μl of 42.0 mM stock solution (1.00 g/100 ml) CoCl$_2$.6H2O; 500 μl of 910.0 mM stock solution (18.0/100 ml) MnCl2.4H2O; 500 μl of 26.0 mM stock solution (0.63 g/100 ml) Na$_2$MoO$_4$.2H$_2$O; bringing up to 500 ml final volume, and filter sterilizing. Vitamin Stock Solution was prepared by adding to 400 mls of water 0.05 g Thiamine HCl; 500 μl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

Fatty acid methyl ester (FAME) analysis was performed on 2 mL samples that were dried using a GeneVac HT-4×. To the dried pellets the following was added: 500 μL of 500 mM KOH in methanol, 200 μL of tetrahydrofuran containing 0.05% butylated hydroxyl toluene, 40 μL of a 2 mg/ml C11:0 free fatty acid/C13:0 triglyceride/C23:0 fatty acid methyl ester internal standard mix and 500 μL of glass beads (425-600 μm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were vortexed for five minutes at 2 krpm and finally centrifuged for three minutes at 1 krpm. The heptane layer was sampled using a Gerstel MPS Autosampler. Quantitation used the 80 µg of C23:0 FAME internal standard.

Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of $r2>0.999$.

Initially, a small-scale medium-throughput assay was utilized to assess productivity levels of the transgenic lines. In the assay, cells were inoculated to an $OD_{730}$ of 0.20 and allowed to grow for 6 days. FAME and TOC levels were measured at 4 days into the assay and at the end of the time-course (day 6). Since cells were grown in T25 shake flasks and the total cell culture volume required was relatively low (~30 ml), at least ten different transgenic lines for each transcription factor could be tested. Most transgenic lines exhibited equal or lower FAME and TOC levels than wild-type. Remarkably, two transgenic lines, GE-5385 and GE-5386, which were both transformed with an overexpression construct for a MYB-like transcription factor, Myb-5256, displayed markedly improved productivity over wild-type in this productivity assay (FIGS. 1A, 1B, and 1C). Each of the two lines, represented in the graphs by dashed lines, displayed higher fatty acid methyl ester content (FAME; FIG. 1A) and higher total organic carbon values (TOC; FIG. 1B) than the wild type strain (dark lines). Interestingly, these two cell lines possessed similar FAME/TOC ratios for wild-type (FIG. 1C), suggesting that the higher FAME levels observed for the mutant could likely be explained by an increase in overall biomass.

Figure 2:
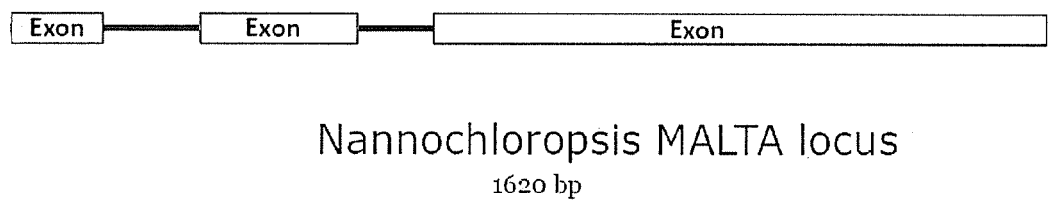
FIG. 2 provides a diagram of the gene structure of the MALTA gene from the *Nannochioropsis gaditana* genome (SEQ ID NO:16). Introns are denoted by thin lines, and exons by dark boxes.

The strains created by transforming wild-type line WT-3730 with a linearized vector designed to overexpress the Myb-5256 (or "MALTA") gene that demonstrated increased biomass productivity were designated GE-5385 and GE-5386. A graphical presentation of the gene structure of the MALTA locus is provided in FIG. 2, demonstrating that the native MALTA gene sequence (SEQ ID NO:16) which was expressed in the transgenic lines includes introns extending from nucleotide 143 to nucleotide 295 of SEQ ID NO:16 and from nucleotide 541 to nucleotide 660 of SEQ ID NO:16. The deduced amino acid sequence encoded by SEQ ID NO:3 (the MALTA cDNA), is set forth in SEQ ID NO:4. A homology search for SEQ ID NO:4 was conducted using the DDBJ/GenBank/EMBL database. Sequence identity and similarity were also determined using STN Express® software (STN International, Germany). A conserved MYB-like DNA-binding domain was identified with an amino acid sequence set forth herein in SEQ ID NO: 2, which corresponds to amino acid residues 52-97 of the amino acid sequence of MALTA protein (SEQ ID NO:4). Further sequence analysis result revealed that the MALTA protein can be considered to be a member of a superfamily of MYB-like DNA-binding domain proteins (Pfam PF00249), based upon high sequence similarity of its MYB-like domain to those of several MYB-like proteins previously reported, including MYB360 from *Nannochioropsis* sp. YJH-2012 (GeneBank Accession No. AGB13670.1) and a MYB-like DNA binding protein/transcription factor-like protein from *Thalassiosira pseudonana* CCMP1335 (GeneBank Accession No. XP 002291033.1). Taken together, these results indicate that SEQ ID NO:3, i.e. the MALTA gene, encodes a MYB-like DNA-binding domain protein from *Nannochioropsis gaditana*.

Example 3

Productivity of Recombinant *Nannochioropsis* Cells that Overexpressed the MALTA Polypeptide (Myb-5256)

qRT-PCR experiments were performed to assess the steady-state mRNA levels of the MALTA transgene Myb-5256 in the *Nannochioropsis* transgenic lines GE-5385 and GE-5386 described in Example 2, as compared to a wild-type control line. The over-expression cassette used to create the GE-5385 and GE-5386 transgenic lines consisted of the Myb-5256 genomic locus (SEQ ID NO:16) driven by an elongation factor promoter from *Nannochioropsis gaditana* (eLF3, SEQ ID NO:6). Cells were grown under standard nitrogen replete conditions and harvested during early stationary phase.

To isolate total RNA from Malta-expressing cells, 10 mLs of an algal cell culture was spun down at 4000×g for 5 minutes and the supernatant was decanted. The pellet was resuspended in 1.8 mL Buffer A (5 mL TLE Grinding Buffer, 5 mL phenol, 1 mL 1-bromo-3-chloropropane and 20 µL mercaptoethanol, where TLE Grinding Buffer includes 9 mL of 1M Tris pH 8, 5 mL of 10% SDS, 0.6 mL of 7.5 M LiCl, and 0.45 M EDTA, in a final volume of 50 L) and transferred to a 2 mL microcentrifuge tube containing approximately 0.5 mL of 200 µm zirconium beads. The tube was vortexed vigorously for 5 min at 4° C. and then centrifuged for 2 min at 11.8×g. The aqueous layer was then removed and pipetted into a new 2 mL tube, to which 1 mL 25:24:1 phenol extraction buffer (25 mL phenol pH 8 or 5.1; 24 mL 1-bromo-3-chloropropane, and 1 mL isoamyl alcohol) was added and the tube was shaken vigorously and centrifuged for 2 min at 11.8×g. After centrifugation, the aqueous layer was removed and pipetted into a new 2 mL centrifuge tube, to which 1 ml 1-bromo-3-chloropropane was added. The tube was shaken and again centrifuged for 2 min at 11.8×g. The aqueous layer was removed to a new tube and 0.356 volumes of 7.5 M LiCl was added. The tube was inverted 10-12 times and stored at −20° C. overnight. The next day, samples were allowed to come to room temperature without mixing and were centrifuged at 16,000×g for 30 minutes. The supernatant was removed and the pellet was washed with 1 mL of ice cold 80% ethanol. The tube was centrifuged for 30 min at 16,000×g and allowed to air dry after the supernatant had been removed. Finally, the RNA pellet was resuspended in 50 µl ultrapure water. The RNA quality was assessed by on-chip gel electrophoresis using an Agilent 2100 Bioanalyzer and RNA6000 LabChip according to manufacturer instructions.

Figure 3:
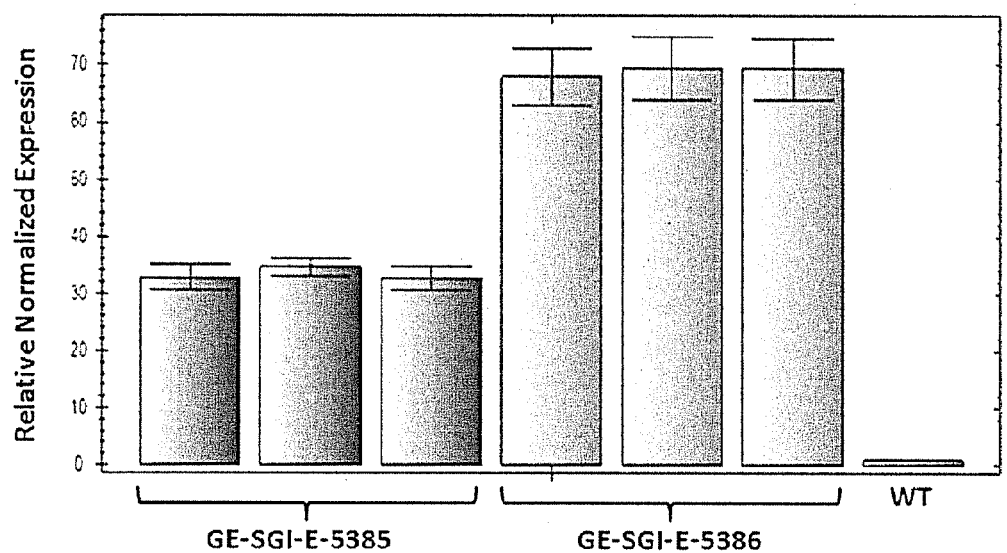
FIG. 3 graphically depicts the results of experiments assessing steady-state mRNA levels of the MALTA transgene Myb-5256 by qRT-PCR in selected *Nannochioropsis* transgenic lines GE-5385 and GE-5386, as compared to a wild-type control line. Normalized expression values were plotted on the y-axis relative to wild-type WT-3730 (WT), which was set at a value of 1. Error bars represent the standard error for 3 technical replicates.

RNA was converted to cDNA using a commercial reverse transcriptase according to the manufacturer's protocol. For PCR, Ssofast EvaGreen Supermix (Bio-Rad, Hercules, Calif.) was used along with gene-specific primers. The PCR reaction was carried out on C1000 Thermal Cycler coupled with a CFX Real-time System (BioRad). Primer and cDNA concentrations were according to the manufacturer's recommendation. Primers for amplifying a sequence of the MALTA transcript were SEQ ID NO:19 and SEQ ID NO:20). Transcript levels for each sample were normalized against a housekeeping gene with consistent expression levels under different culture conditions (1T5001704; SEQ ID NO:21; primer sequences were SEQ ID NO:22 and SEQ ID NO:23) and relative expression levels were calculated using the ddCT method using BioRad's CFX Manager software. FIG. 3 shows normalized expression values plotted on the y-axis relative to wild-type (WT), where expression of Myb-5256 was equal to 1 for WT. The error bars represent the standard error for 3 technical replicates. As expected, both strains were found to over-express the MALTA transgene at significantly higher levels over the wild-type parent (FIG. 3), suggesting that the observed increases in FAME and TOC levels of GE-5385 and GE-5386 as described in Example 2 were due to over-expression of MALTA.

Figure 4:
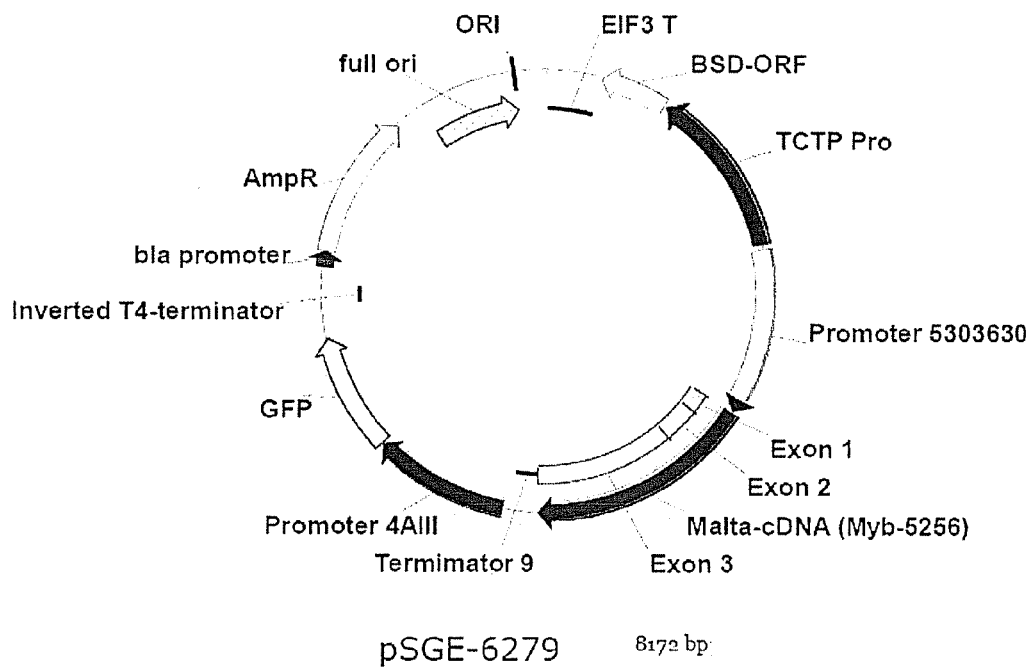
FIG. 4 is a schematic representation of the vector pSGE-6279, used for overexpressing the MYB-like transcription factor MALTA cDNA (SEQ ID NO:3) in *Nannochloropsis*.

To further validate this hypothesis, an additional expression vector was constructed to place expression of the MALTA cDNA under the control of the *Nannochloropsis* promoter p5303630 (SEQ ID NO:7), which corresponded to a *Nannochloropsis* gene encoding a 60S ribosomal protein L24 and had been previously identified to be a strong constitutive promoter in *Nannochloropsis* cells. In this expression vector, the cDNA sequence of MALTA (SEQ ID NO:3) was fused to the constitutive promoter p5303630 and terminator element Term9 from *Nannochloropsis* (SEQ ID NO:8), and the resulting p5303630-MALTA-Term9 cassette was cloned into a pTRUC vector backbone. The final vector, which was named pSGE-6279 (FIG. 4), contained a GFP gene (SEQ ID NO:18) that allowed for selection of stable transgenic lines with full penetrance, i.e. expression across the entire cell population of a culture. After transformation of pSGE-6279 into the wild-type *Nannochloropsis* strain WT-3730, the ensuing lines were screened for GFP fluorescence by flow cytometry. Clones that failed to exhibit a Gaussian distribution of GFP fluorescence indicating full penetrance were discarded, while those that did were advanced for qRT-PCR analysis of MALTA expression.

Figure 5:
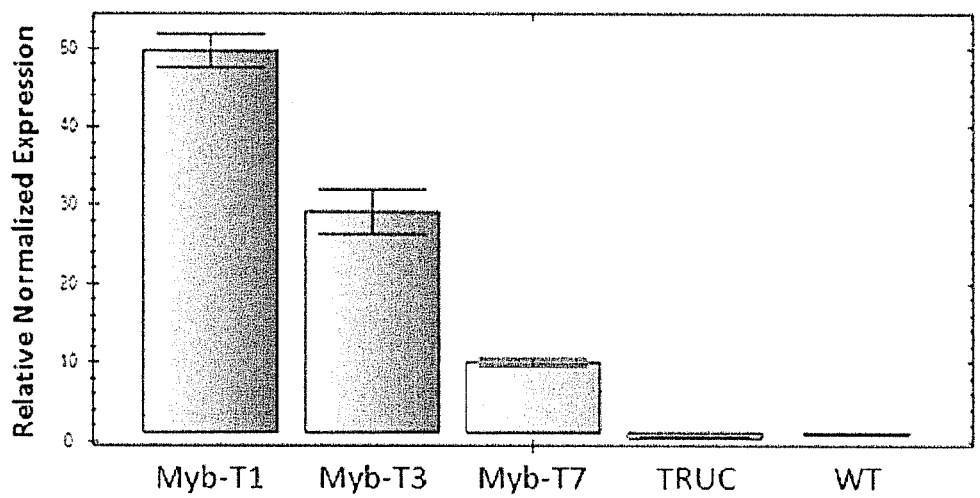
FIG. 5 graphically depicts the results of experiments assessing steady-state mRNA levels of the Myb-5256 transgene (cDNA) in three *Nannochloropsis* transgenic lines (Myb-T1, Myb-T3, Myb-T7), wild-type control line WT-3730 (WT) and empty vector control line (TRUC), as quantitated by qRT-PCR. Normalized expression values were plotted relative to WT, so that expression of Myb-5256 in WT was equal to 1. Error bars represent the standard error for 3 technical replicates.

Three independent *Nannochloropsis* transgenic strains containing the p5303630-MALTA-Term9 cassette, named Myb-T1, Myb-T3, and Myb-T7, were selected for qRT-PCR analyses to assess the steady-state mRNA levels of the MALTA transgene. Cells were grown under standard replete conditions and harvested during early stationary phase. FIG. 5 shows normalized expression values plotted on the y-axis relative to the wild-type (WT) expression value; expression of Myb-5256 (MALTA) was set at 1 for WT. Normalization was calculated against a house keeping gene (1T5001704; SEQ ID NO:21). Error bars represent the standard error for 3 technical replicates. As expected, qRT-PCR results indicated that the three strains tested were over-expressing Myb-5256/MALTA at considerably higher levels (10 to 50 fold) over wild-type control (FIG. 5). Also assayed as negative control in this experiment was a transgenic *Nannochloropsis* strain transformed with an empty cloning vector backbone (TRUC), in which MALTA overexpression was not observed, as expected.

Figure 6A:
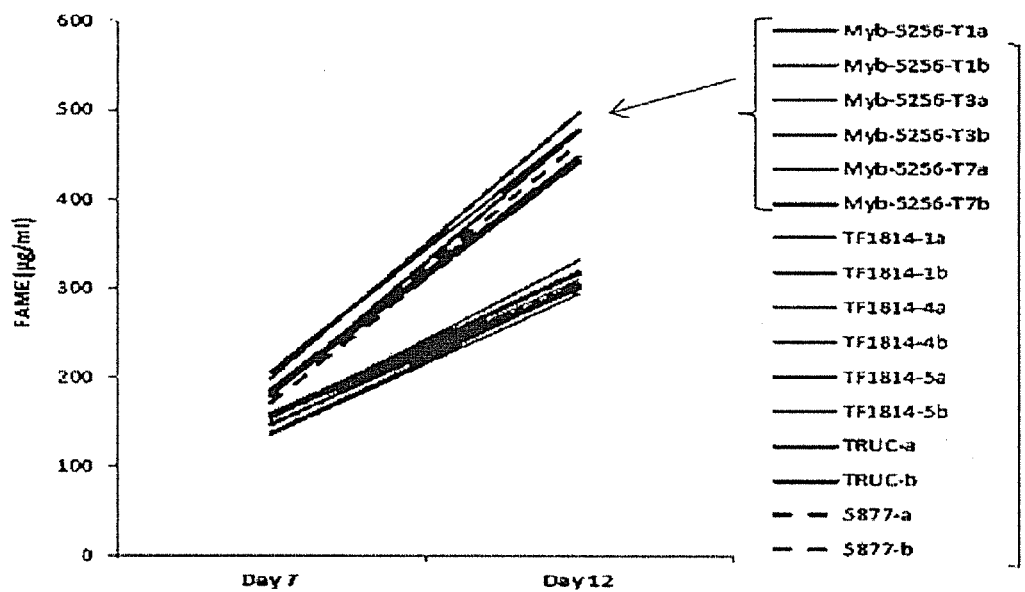
FIGS. 6A and 6B illustrate the results of experiments assessing productivity level of fatty acid methyl esters (FAME) (FIG. 6A) and total organic carbon (TOC) (FIG. 6B) values for three transgenic strains and controls on days 7 and 12 in a standard productivity assay. The graphs represent the amounts of fatty acid methyl esters (FAME) and total organic carbon (TOC) produced by three transgenic *Nannochloropsis* strains overexpressing MALTA (Myb-T1, Myb-T3, Myb-T7); as well as a positive control line containing a different mutation (5877; dashed lines) previously identified as having higher productivity levels than wild type was included as a positive control in this experiment. Also assayed as negative controls in these experiments were *Nannochloropsis* transgenic strains transformed with either an empty cloning vector backbone (TRUC; black lines) or with an expression vector containing a different *Nannochloropsis* transgene under control of the same promoter (TF 1814; gray lines). Duplicate cultures of each line are labeled a and b.
Figure 6B:
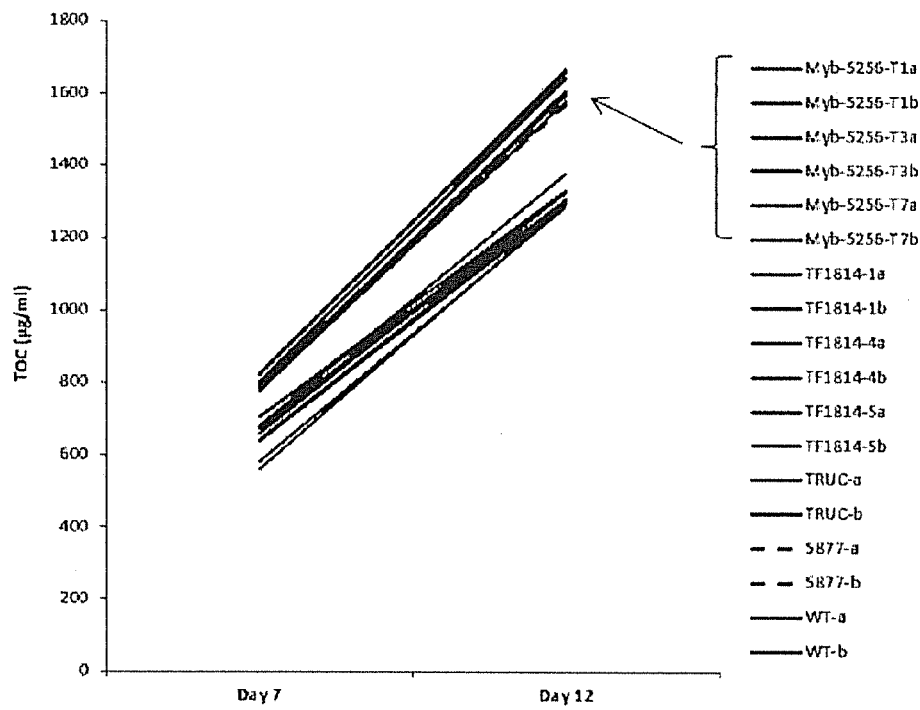

The confirmed over-expression lines (Myb-T1, Myb-T3, and Myb-T7) were tested for FAME and TOC levels to determine whether over-expression of the cDNA sequence encoding MALTA also resulted in increased productivity. For this purpose, 100 mL-cell cultures were inoculated to an $OD_{730}$ of 0.25 (in T75 shake flasks). FAME and TOC levels were measured 7 days into the experiment and at the end of the experiment (day 12). FIGS. 6A and 6B summarize the results of experiments assessing productivity level of fatty acid methyl esters (FAME, FIG. 6A), total organic carbon (TOC, FIG. 6B) values for three transgenic strains and controls on days 7 and 12 in a standard productivity assay. Each of the transgenic lines was grown in duplicate (duplicate cultures are labeled a and b). Also assayed as negative controls in these experiments were *Nannochloropsis* transgenic strains transformed with either an empty cloning vector backbone (TRUC) or with an expression vector containing a different *Nannochloropsis* transgene (named TF 1814) under control of the same promoter p5303630. In addition, a *Nannochloropsis* strain (GE-5877) previously identified to reproducibly produce higher productivity levels than wild-type was used as a positive control in this experiment. As previously observed, the positive control GE-5877 grew faster than wild-type and recorded higher FAME and TOC values. The three transgenic lines over-expressing MALTA were found to also outperform the wild-type and showed on par or higher values than the positive control (FIGS. 6A and 6B). Moreover, three other transgenic lines corresponding to a different transcription factor (TF 1814), which was driven under the same promoter and cloned into the same backbone as MALTA was, did not show any improvements over wild-type or the empty vector control.

Figure 7:
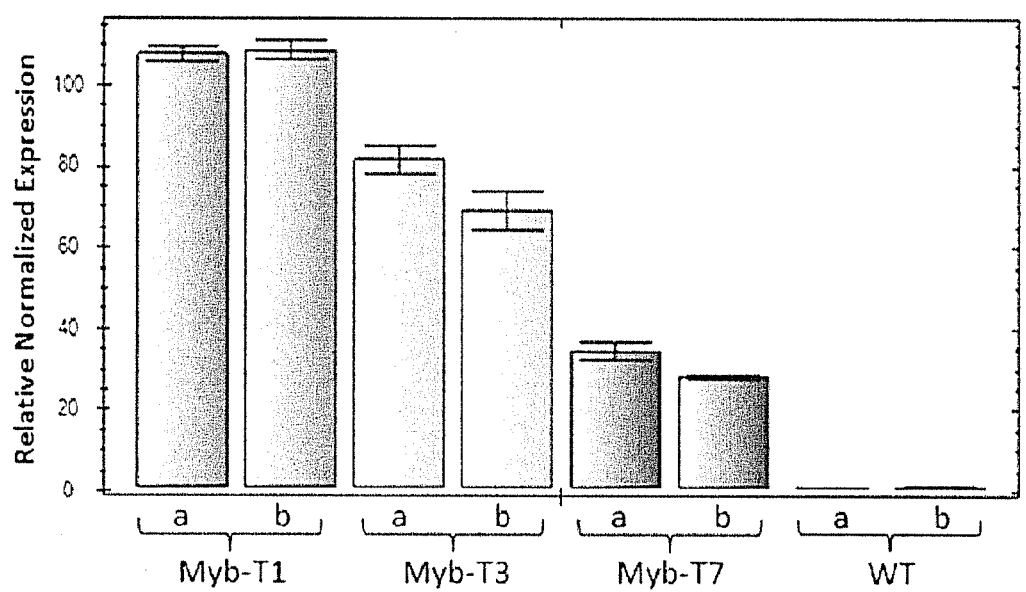
FIG. 7 graphically depicts the results of experiments assessing steady-state mRNA levels of the Myb-5256 transgene in three *Nannochloropsis* transgenic lines (Myb-T1, Myb-T3, Myb-T7) and wild-type control line (WT), by qRT-PCR at the end of the productivity assay of FIGS. 6A and 6B. Normalized expression values were plotted relative to the wild-type technical replicate WT-a; therefore expression of Myb-5256 in WT-a was equal to 1. Error bars represent the standard error for 3 technical replicate. Biological duplicates of each line are labeled a and b.

To confirm that MALTA was still over-expressed at the end of the experiment, gene expression levels for MALTA were measured again on day 12 of the productivity assay (FIG. 7). Once again, steady-state mRNA levels of the MALTA transgene, as determined by qRT-PCR, demonstrated up-regulation of MALTA in the transgenic lines compared to wild-type. Altogether, these data strongly suggest that over-expression of the MYB-like transcription factor MALTA in *Nannochloropsis* results in improved growth rates and higher FAME productivity.

Example 4

Genetic Transformation of *Tetraselmis* by Particle Bombardment

*Tetraselmis* transformation is carried out by particles bombardment using the Bio-Rad Helio™ PDS-1000/He gene gun apparatus according to manufacturer's instructions with minor modifications.

Plasmid DNA isolated from overnight *E. coli* cultures is quantitated and digested overnight with an enzyme appropriate for linearization. The plasmid includes a nucleic acid sequence encoding the polypeptide of SEQ ID NO:4 operably linked to the *Tetraselmis* GAPDH promoter of SEQ ID NO:9 (or any of the promoters provided in U.S. Ser. No. 13/693,585, filed Dec. 4, 2012, and incorporated herein by reference in its entirety) and the GAPDH terminator (SEQ ID NO:10). The plasmid can further include a selectable marker, such as, for example, the *Streptoalloteichus hindustanus* (Sh) ble gene conferring Zeocin-resistance and codon-optimized for expression in *Chlamydomonas reinhardtii* (SEQ ID NO:11), which can be operably linked to an algal promoter, such as, for example, the *Tetraselmis* actin promoter (SEQ ID NO:12) and the *Tetraselmis* actin terminator fragment (SEQ ID NO:13).

Gold particles are prepared as follows: Gold microcarriers (Bio-Rad Cat#165-2262) are weighed into a 1.5 mL tube. For 40 shots at 0.5 mg gold/shot, typically 20 mg of gold microcarriers is used. Following addition of 100 µL 0.05M spermidine, the tube is vortexed, and may optionally be sonicated for approximately 5 seconds. Plasmid DNA is then added to the tube, followed by brief vortexing. While vortexing, 100 uL 1M $CaCl_2$ is added drop-wise. The volume of plasmid varies depending on the desired amount of DNA per shot. The tube is then incubated at room temperature for 10 minutes. The gold preparation is centrifuged briefly for 10-15 seconds to discard the supernatant. The pellet is washed three times with 1 mL ethanol, with vortexing and spinning down between each wash. The pellet is then resuspended in a 2.5 mL ethanol/PVP solution (a mixture of 2.5 mL ethanol and 1.25 uL of 20 mg/mL PVP stock in ethanol), followed by sonication for 5 seconds.

Two days prior to shooting, a culture of a *Tetraselmis* strain, WT-105, is inoculated at $5\times10^5$ cells/mL in PM032 media, and cells are grown at 25° C., 1% $CO_2$ on a rotation share set at 125 rpm on a 16:8 light:dark cycle. In a typical protocol of particle bombardment, algal cells are first concentrated and plated prior to transformation shootings. Algal cells are counted using Accuri cytometer. A cell count of at $1\times10^6$ cells/mL is preferable. Cells are then concentrated to $5\times10^7$ cells/mL before plating 200 uL of concentrated cells onto PM032 1.5% agar plates within a 4 cm-diameter circle. A total of 15 circles (e.g. a total of $1.5\times10^8$ cells) are placed on a single 22×22 cm plate and allowed to dry. The distance between the stopping ring and the target (microalgal cells) is 5 cm. Plates are placed on the bench to recover for approximately 24 hours.

PM032 medium is 10×F/2 replete medium that includes 8.8 mM $NaNO_3$ and 0.4361 mM $NaH_2PO_4.H_2O$, 10×F/2 Trace metals, and 10×F/2 Vitamins and and can be made by mixing 1.3 ml/L of ProLine F/2 Part A and 1.3 ml/L of ProLine F/2 Part B in 800 ml seawater. The solution is stirred thoroughly, brought up to 1 liter with distilled water, and filter sterilized using a 0.22 µm filter.

After transformation, algal cells are recovered by adding approximately 20 mL of PM032 media to the plate. Algal cells are scrapped with inoculating loop to resuspend cells in liquid PM032 media. A 25 mL serological pipette is used to remove as much liquid media as possible from plate and place in a 50 mL conical tube. An additional 20 mL of PM032 media is added to the plate to recover any remaining algae and transfer this liquid media to the conical tube. Cells are pelleted by centrifugation at 3,000×g for 5 minutes, resuspended in 4 mL PM032, and then spread with autoclaved glass beads onto two 22×22 cm selection plates. Plates are allowed to dry, wrapped in micropore tape and placed on light shelves. Algal colonies typically appear after 1-2 weeks.

Example 5

Genetic Transformation of *Cyclotella* by Particle Bombardment

Plasmid DNA isolated from overnight *E. coli* cultures is quantitated and digested overnight with an enzyme appropriate for linearization. The plasmid includes a nucleic acid sequence encoding the polypeptide of SEQ ID NO:4 operably linked to the *Cyclotella* Accase promoter of SEQ ID NO:14 (or any of the promoters provided in Niu et al. (2012) BioTechniques Rapid Dispatches doi:10.2144/000113881). The plasmid can further include a selectable marker, such as, for example, the *Streptoalloteichus hindustanus* (Sh) ble gene conferring Zeocin-resistance and codon-optimized for expression in *Chlamydomonas reinhardtii* (SEQ ID NO:11), which can be operably linked to an algal promoter, such as, for example, any provided in Paulsen & Kroger *FEBS J.* 272: 3413-23 or Siaut et al. *Gene* 406:23-35.

Cultures of a diatom *Cyclotella* strain, WT-293, are grown in PM101 liquid media in high light growth conditions, 30° C., under a 14:10 diel cycle (Adaptis incubator). Cells at exponential growth phase ($<1\times10^6$ cells/nil) are pelleted by centrifugation (20 minutes, 5000 g, 20° C.), resuspended in ~20 mls of 0.5M Osmoticum (0.25M Sorbitol+0.25M Mannitol) for a high concentration of cells (~$1\times10^8$ cells/ml), and determined cell count. Approximately $3\times10^7$ cells are spread onto the center ⅔rd of a PM101 agar plate. PM101 media is identical to PM024 described in Example 1, except for it contains 10 mM $NaNO_3$, 0.417 mM $K_2HPO_4$ and 1 mM $Na_2SiO_3$. Plates are then allowed to dry in sterile hood.

The microcarriers are tungsten particles M17 (Bio-Rad Cat#165-2267). Microcarriers are prepared according to the protocol of the supplier (Bio-Rad), and include the following steps. (1) Weigh 60 mg of tungsten particles into "Treff" microtubes (VWR Cat.#101100-388); (2) Add 1 ml 70% Ethanol and vortex for 5 minutes at room temperature; (3) Store the tube on the bench top for 15 minutes; (4) Centrifuge in picofuge for 5 seconds; (5) Remove supernatant and resuspend in 1 ml sterile $H_2O$; (6) Vortex for 1 minute and then store the tube on the bench top for 1 minute; (7) Centrifuge in picofuge for 5 seconds; (8) Repeat H2O wash (steps 5-7) three more times; and (9) Remove supernatant after final wash and resuspend particles in 1 ml of sterile 50% glycerol.

In most *Cyclotella* transformation experiments, the DNA binding procedure involves the following steps. (1) While vortexing stock solution of microcarrier particles, remove a 50 µl aliquot of beads (i.e., approximately 3 mg) and transfer to a fresh microfuge tube; (2) To the aliquot, add plasmid DNA (3 mg). Plasmid DNA is preferably at a high concentration (~1 mg/ml); (3) Add 50 ml of 2.5M $CaCl_2$; (4) Add 20 µl of 0.1M spermidine (Fluka 05292-1ML-F); (5) continue to vortex tube for an additional 3 minutes; (6) Store the tube on the bench top for 1 minute; (7) Pellet particles for 2 seconds in picofuge; (8) Remove supernatant and carefully layer with 140 µl of 70% Ethanol; (9) Remove supernatant and carefully layer with 140 µl of 100% Ethanol; and (10) Remove supernatant and resuspend in 30 µl 100% Ethanol.

The macrocarriers (Bio-Rad Cat#165-2335) are prepared by setting up X-segmented Petri dishes (VWR Cat#25384-308) with desiccant in each quadrant. Autoclaved macrocarrier/macrocarrier holder is then placed in each quadrant atop desiccant. Approximately, 10 µl of DNA/Beads is dispensed onto center of macrocarrier and allowed to dry.

A typical protocol of particle bombardment includes the following steps. (1) Dip rupture disk (Bio-Rad #165-2330) into isopropanol and place in rupture disk retaining cap; (2) Secure retaining cap to end of gas acceleration tube and tighten with torque wrench; (3) Load stopping screen (Bio-Rad Cat#165-2336) and macrocarrier into microcarrier launch assembly; (4) Place microcarrier launch assembly into chamber; (5) Place target shelf with agar plate containing cells on Level 2 in chamber and close door; (6) Apply vaccum and hold at 10 Hg; (7) Depress FIRE button until rupture disk bursts; (8) Release vaccum, open door and remove agar plate; (9) Unload macrocarrier and stopping screen from launch assembly; (10) Unload spent rupture disk. Helium pressure in a Biolistic PDS-1000-HE particle delivery system used in these transformation experiments is set at approximately 2,000 psi, and the distance between rupture disk retaining cap and microcarrier launch assembly is 0.5 cm, which can be verified using hexagonal gap tools.

After bombardment, diatom cells are recovered as follows. Cells are scraped from agar plate by adding ~5 ml media and scraping with L-shaped spreader; transferred to 50 ml PM101 media in a 125 ml flask, which is then incubated in approximately 50 E light, 30° C., 1% $CO_2$ and cells are allowed to recover for 24 hrs. At this step, cell counts can be determined before being pelleted by centrifugation. Supernatant is decanted by leaving ~1-2 ml media. Cell culture is resuspended in remaining media and plated onto Antibiotic plates (max. $2\times10^7$ cells/plate). Plates are then wrapped with micropore tape and placed under high light. Diatom colonies typically appear after 1-2 weeks.

Example 6

Molecular Characterization and Evaluation of Recombinant Algal Cells

The ability of a recombinant MALTA-like polypeptide to confer modulated biomass productivity is assessed in a number of ways. Following introduction of heterologous foreign DNA into algal cells, the transformation or integration of heterologous gene in the algal genome is confirmed by a number of methods such as analysis of nucleic acids, proteins and metabolites associated with the integrated gene. For example, PCR analysis is a rapid method, among others, to screen transformed cells (Sambrook and Russell, 2001, supra). PCRs are carried out using oligonucleotide primers specific to the antibiotic-tolerance gene of interest or to the transformation vector backbone, etc.

Algal transformants derived from transformation experiments are also confirmed by Southern blot analysis of genomic DNA (Sambrook and Russell, 2001, supra). In general, total DNA is extracted from the transformant by using a procedure described previously (see, e.g. European Pat. Appl. No. EP2090648A1), digested with appropriate restriction enzymes, size-fractionated in an agarose gel and transferred to a nitrocellulose or nylon membrane. The membrane or "blot" is then probed with, for example, a nonradioactive DIG-labeled target DNA fragment to confirm the integration of introduced gene into the plant genome according to standard techniques ("Genius" DIG-based system, Boehringer Mannheim Biochemicals GmbH, Germany; Sambrook and Russell, 2001, supra), or a radiolabeled $^{32}P$ probe may be used for Southern blot analysis.

Expression of the MALTA-like transgene can be evaluated by PCR. Western blot, biochemical assays and the like can also be carried out on the transgenic algae to confirm the presence of protein encoded by the MALTA-like gene by standard procedures (e.g., Sambrook and Russell, 2001, supra) using antibodies that bind to one or more epitopes present on the MALTA protein.

The effects of the exogenous MALTA-like gene can be investigated using the productivity assays provided herein, or similar assays in which the recombinant algal cells that overexpress a MALTA-like gene or a gene encoding a protein homologous to a MALTA-like protein are cultured and analyzed for production or accumulation of a product. The product can be, as nonlimiting examples, a carbohydrate, a polymer, an alcohol, a sugar, a vitamin, a small molecule, a polyketide, a pigment, a colorant, a peptide, a protein, or a lipid. Alternatively or in addition, a recombinant cell that overexpresses a MALTA-like gene or an ortholog thereof can be tested for increased growth rate and/or biomass accumulation.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives, and equivalents are within the scope of the invention as described and claimed herein.

All publications and patent applications mentioned in this specification are herein incorporated by reference to the same extent as if each individual publication or patent application was specifically can individually indicated to be incorporated by reference. Information sources referenced herein include, for example, World Wide Web browser-inactive page addresses. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

What is claimed is:

1. An isolated or recombinant nucleic acid molecule comprising a nucleic acid sequence encoding a polypeptide that comprises an amino acid sequence having at least 95% sequence identity to the amino acid sequence of SEQ ID NO:4, wherein the nucleic acid molecule is operably linked to a heterologous nucleic acid sequence, wherein the encoded polypeptide belongs to pfam PF00249 and has DNA binding and transcription factor activity, and further wherein elevated expression of the isolated or recombinant nucleic acid molecule in a recombinant *Nannochloropsis* cell results in increased biomass productivity, increased lipid productivity, or increased growth rate of the recombinant *Nannochloropsis* cell as compared to a control recombinant *Nannochloropsis* cell that does not express the isolated or recombinant nucleic acid molecule.

2. The isolated or recombinant nucleic acid molecule according to claim 1, wherein the heterologous nucleic acid sequence comprises a regulatory element.

3. The isolated or recombinant nucleic acid molecule according to claim 1, wherein the polypeptide comprises an amino acid sequence that has at least 90% sequence identity to the amino acid sequence of SEQ ID NO:2.

4. A vector comprising the isolated or recombinant nucleic acid molecule according to claim 1.

5. A recombinant algal or heterokont cell comprising the isolated or recombinant nucleic acid molecule of claim 2.

6. The recombinant algal or heterokont cell according to claim 5, wherein the recombinant algal or heterokont cell is a recombinant heterokont cell.

7. The recombinant heterokont cell according to claim 6, wherein the recombinant heterokont cell is of a genus selected from the group consisting of *Labryinthula, Labry-* inthuloides, Thraustochytrium, Schizochytrium, Aplanochytrium, Aurantiochytrium, Oblongichytrium, Japonochytrium, Diplophrys, and Ulkenia.

8. The recombinant algal or heterokont cell according to claim 5, wherein the recombinant algal or heterokont cell is a recombinant algal cell.

9. The recombinant algal cell according to claim 8, wherein the recombinant algal cell is of a genus selected from the group consisting of Achnanthes, Amphiprora, Amphora, Ankistrodesmus, Asteromonas, Boeketovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragitaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicuta, Neochloris, Nephrochloris, Nephroselmis, Nitzschia, Ochromonas, Oedogonium, Oocystis, Ostreococcus, Parachloretta, Parietochloris, Pascheria, Pavlova, Pelagomonas, Phceodactylum, Phagus, Picochlorum, Platymonas, Pteurochrysis, Pleurococcus, Prototheca, Pseudochlorelta, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria, and Volvox.

10. The recombinant host cell according to claim 9, wherein the recombinant algal cell is of a genus selected from the group consisting of Cyclotella, Nitzschia, Pavlova, Phceodaclylum, and Thalassiosira.

11. The recombinant algal cell according to claim 9, wherein the recombinant algal cell is of genus selected from the group consisting of Eustigmatos, Monodus, Nannochloropsis, and Vischeria.

12. The recombinant algal cell according to claim 11, wherein the recombinant algal cell is a Nannochloropsis cell.

13. A method for producing a biomass or a lipid, comprising culturing the recombinant algal or heterokont cell according to claim 5 and producing the biomass or the lipid therefrom.

14. The method according to claim 13, further comprising isolating the biomass or the lipid from the culture.

15. The method according to claim 13, wherein the recombinant algal or heterokont cell is a recombinant algal cell.

16. The method according to claim 15, wherein the recombinant algal cell is of a genus selected from the group consisting of Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricmphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragitaria, Fragilaropsis, Gloeothamnion, Haematococcus, I-Iantzschia, Heterosigma, Hymenomonas, Isochrysis, Lepocinclis, Micractinium, Monodus, Monora_phidium, Nannochloris, Nannochtoropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phceodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thatassiosira, Tribonema, Vaucheria, Viridielta, Vischeria, and Volvox.

17. The method according claim 16, wherein said culturing is under photoautotrophic conditions.

18. The isolated or recombinant nucleic acid molecule according to claim 2, wherein the regulatory element comprises a promoter.

19. The recombinant algal or heterokont cell according to claim 5, wherein the regulatory element comprises a promoter.

* * * * *